(12) United States Patent
Fritz et al.

(10) Patent No.: US 12,420,165 B2
(45) Date of Patent: *Sep. 23, 2025

(54) METHOD AND DEVICE FOR CONTROLLING ACOUSTIC FEEDBACK DURING A PHYSICAL EXERCISE

(71) Applicant: MAX-PLANCK-GESELLSCHAFT ZUR FÖRDERUNG DER WISSENSCHAFTEN E.V., Munich (DE)

(72) Inventors: Thomas Fritz, Karlsruhe (DE); Eric Busch, Leipzig (DE); Silvio Borchardt, Leipzig (DE); Dirk Gummel, Leipzig (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/232,684

(22) Filed: Aug. 10, 2023

(65) Prior Publication Data

US 2023/0381627 A1  Nov. 30, 2023

Related U.S. Application Data

(63) Continuation of application No. 16/641,982, filed as application No. PCT/EP2018/073016 on Aug. 27, 2018, now Pat. No. 11,731,025.

(30) Foreign Application Priority Data

Aug. 25, 2017  (EP) ..................... 17187876

(51) Int. Cl.
*A63B 71/06* (2006.01)
*A61H 3/00* (2006.01)
(Continued)

(52) U.S. Cl.
CPC ......... *A63B 71/0622* (2013.01); *A61H 3/008* (2013.01); *A63B 21/00043* (2013.01);
(Continued)

(58) Field of Classification Search
CPC .......... A63B 71/0622; A63B 21/00043; A63B 21/02; A63B 24/0062; A63B 24/0075;
(Continued)

(56) References Cited

U.S. PATENT DOCUMENTS 4,776,323 A  10/1988  Spector
4,957,282 A  9/1990  Wakefield
(Continued)

FOREIGN PATENT DOCUMENTS

CN  102314557  1/2012
GB  1208651  10/1970
WO  2011/147934  12/2011

OTHER PUBLICATIONS

International Search Report and Written Opinion for PCT Application No. PCT/EP2018/073016 mailed Nov. 30, 2018.
(Continued)

*Primary Examiner* — Sundhara M Ganesan
(74) *Attorney, Agent, or Firm* — Branch Partners PLLC; Bruce E. Black

(57) ABSTRACT

Techniques for providing acoustic feedback are disclosed. Several audio clips have a synchronized beat. A sensor signal received from a sensor has a sensor signal range divided by first and second thresholds into at least three sensor signal sub-ranges. An audio signal is output in response to the received sensor signal, the output audio signal comprising one or more of the audio clips. If the received sensor signal exceeds the first threshold, at least one of the one or more audio clips is discontinued and/or at least one additional audio clip of the audio clips is initiated (Continued)

in synchronization with the one or more audio clips. If the received sensor signal falls below the second threshold, at least one of the one or more audio clips is discontinued and/or at least one additional audio clip of the audio clips is initiated in synchronization with the one or more audio clips.

22 Claims, 10 Drawing Sheets

(51) Int. Cl.
  *A63B 21/00* (2006.01)
  *A63B 21/02* (2006.01)
  *A63B 24/00* (2006.01)
  *G06F 3/16* (2006.01)
  *G10H 1/00* (2006.01)
(52) U.S. Cl.
  CPC .......... *A63B 21/02* (2013.01); *A63B 24/0062* (2013.01); *A63B 24/0075* (2013.01); *A63B 71/0686* (2013.01); *G06F 3/165* (2013.01); *G10H 1/0008* (2013.01); *A63B 2071/0625* (2013.01); *A63B 2220/802* (2013.01); *A63B 2220/806* (2013.01); *A63B 2220/836* (2013.01); *G10H 2220/201* (2013.01); *G10H 2220/371* (2013.01); *G10H 2220/395* (2013.01); *G10H 2250/035* (2013.01)
(58) Field of Classification Search
  CPC ........ A63B 71/0686; A63B 2071/0625; A63B 2220/802; A63B 2220/806; A63B 2220/836; A63B 24/00; A63B 2230/00; A61H 3/008; G06F 3/165; G10H 1/0008; G10H 2220/201; G10H 2220/371; G10H 2220/395; G10H 2250/035; G10H 1/40; G10H 1/46; G16H 20/30
  See application file for complete search history.

(56) References Cited

U.S. PATENT DOCUMENTS

| 5,785,631 | A | 7/1998 | Heidecke |
| 6,428,451 | B1 | 8/2002 | Hall |
| 8,269,093 | B2 | 9/2012 | Naik et al. |
| 9,697,813 | B2 | 7/2017 | Lyske |
| 11,731,025 | B2 * | 8/2023 | Fritz ................. A63B 24/0075 482/3 |
| 2006/0136173 | A1 | 6/2006 | Case et al. |
| 2007/0060446 | A1 | 3/2007 | Asukai et al. |
| 2008/0188354 | A1 | 8/2008 | Pauws et al. |
| 2008/0254946 | A1 | 10/2008 | Pauws et al. |
| 2010/0075806 | A1 | 3/2010 | Montgomery |
| 2013/0312589 | A1 | 11/2013 | MacPherson |
| 2014/0254831 | A1 | 9/2014 | Patton |
| 2016/0346584 | A1 | 12/2016 | Schneider et al. |
| 2016/0372095 | A1 | 12/2016 | Lyske |
| 2016/0372096 | A1 | 12/2016 | Lyske |

OTHER PUBLICATIONS

Thomas H. Fritz et al: "Musical feedback during exercise machine workout enhances mood" Frontiers in Psychology, vol. 4, Dec. 10, 2013 (Dec. 10, 2013), XP055446477, D01: 10.3389/fpsyg.2013.00921.

Extended European Search Report for EP Patent Application No. 17187876.2 mailed Mar. 15, 2018.

Official Communication for U.S. Appl. No. 16/641,982 mailed Oct. 5, 2022.

* cited by examiner

METHOD AND DEVICE FOR CONTROLLING ACOUSTIC FEEDBACK DURING A PHYSICAL EXERCISE

CROSS-REFERENCE TO RELATED APPLICATIONS

This present application is a continuation of U.S. patent application Ser. No. 16/641,982, filed Feb. 25, 2020, which issued as U.S. Pat. No. 11,731,025, which is a U.S. national stage application of PCT Application No. PCT/EP2018/073016, filed Aug. 27, 2018, which claims priority to European Patent Application No. 17187876.2, filed Aug. 25, 2017, all of which are hereby incorporated by reference in their entireties.

TECHNICAL FIELD

The invention relates to techniques for controlling acoustic feedback during a physical exercise. The invention relates in particular to methods and devices for controlling acoustic feedback based on characteristics of a physical exercise captured using a sensor.

BACKGROUND

Physical exercise activities may be performed individually or in a group environment and are popular and encouraged to improve the physical fitness and health. Techniques that keep users motivated during the performance of a physical exercise have received considerable attention in view of the beneficial effects of regular physical exercise on the health. A user's lack of motivation to repeat a given exercise may cause the user to discontinue his or her physical training activities, which is undesirable. Manufacturers of exercise equipment have an interest in providing audio signals during the exercise to at least partially compensate for the monotony and repetitive character that is associated with at least some physical exercises.

US 2010/0075806 A1 discloses a method for evaluating movement of a user and providing biofeedback. The method comprises: setting a reference point for movement by the user, whereby the reference point corresponds to a reference rhythm; providing the reference rhythm to the user to assist the user in maintaining the reference point; sensing the user's movement; comparing the user's movement to the reference point movement; and alerting the user that the user's movement is away from the reference point by modifying the reference rhythm to a modified rhythm.

US 2007/0060446 A1 discloses a sound-output-control device including an acquisition unit which acquires an anaerobic threshold, a reception unit which receives an input about exercise intensity, a calculation unit which calculates a value indicating a target heart rate of a user on the basis of the acquired anaerobic threshold and the received exercise-intensity input, a detection unit which detects a value indicating the current tempo of a physical exercise done by the user, and a control unit that controls a sound output on the basis of a result of a comparison of the target heart-rate value calculated by the calculation unit and the current physical-exercise-tempo value detected by the detection unit, so as to lead a heart rate of the user so that the heart rate of the user attains the target heart rate.

While conventional feedback techniques such as the ones disclosed in US 2010/0075806 A1 and US 2007/0060446 A1 can trigger the user to perform an exercise in such a way that certain physiological target conditions, such as a target heart rate, are attained, this kind of feedback provides little benefit in maintaining or even increasing the user's motivation. Moreover, it may be a considerable challenge for many users to synchronize the rhythm of the physical exercise with the musical beat.

Devices and methods that provide an acoustic output that is controllable by the user and that is affected by one or several parameters of the user's physical exercise may offer additional motivation. Such techniques allow the user to generate sound that is controlled by one or several parameters of the physical exercise. WO 2011/147934 A1 discloses an exercise device which comprises means for generating a control signal for an audio device, the control signal being at least partially based on the actual configuration of the exercise device.

U.S. Pat. No. 9,697,813 B2 discloses a system that permits identified musical phrases or themes to be synchronized and linked into changing real-world events. The synchronization includes a seamless musical transition that is achieved using a timing offset.

US 2014/0254831 A1 discloses an adaptive music playback system. The system includes a composition system that receives information corresponding to user activity levels. The composition system modifies the composition of a song in response to changes in user activity. The modifications are made according to a set of composition rules to facilitate smooth musical transitions.

When acoustic feedback is provided that helps users to keep motivated during a physical exercise, it is desirable that the user is enabled to easily generate interesting acoustic feedback, without requiring extensive prior experience with the acoustic feedback generation system. It would be particularly desirable to provide techniques that offer a steep increase at the start of a learning curve and/or that decrease the time required for the user to learn how to create satisfactory acoustic feedback during a physical exercise. Alternatively or additionally, the space of possible sounds and combinations to be explored by the user during an exercise session should be large enough to allow the user to stay motivated while not making the generation of motivating acoustic patterns unduly complicated.

SUMMARY

In view of the above, it is an object of the invention to provide improved methods, devices, and systems for controlling acoustic feedback during a physical exercise. In particular, it is an object to provide methods, devices, and systems for controlling acoustic feedback during a physical exercise that enable the user to easily generate interesting acoustic feedback without requiring the user to synchronize a beat of the acoustic feedback with the movements carried out during the physical exercise. Alternatively or additionally, it is an object to provide methods, devices, and systems for controlling acoustic feedback during a physical exercise that enable the user to explore a large space of possible sounds and combinations of sounds during an exercise.

According to the invention, a method, a device, and a computer program as recited in the independent claims are provided. The dependent claims define preferred embodiments.

A method of providing acoustic feedback during a physical exercise comprises:

providing several audio clips having a synchronized beat;

receiving a sensor signal from a sensor, the sensor signal having a sensor signal range divided by first and second thresholds into at least three sensor signal sub-ranges; and outputting an audio signal in response to the received sensor signal, the output audio signal comprising one or more of the audio clips.

If the received sensor signal exceeds the first threshold, at least one of the one or more audio clips is discontinued and/or at least one additional audio clip of the audio clips is initiated in synchronization with the one or more audio clips. If the received sensor signal falls below the second threshold, at least one of the one or more audio clips is discontinued and/or at least one additional audio clip of the audio clips is initiated in synchronization with the one or more audio clips.

The several audio clips may respectively have a beat that is synchronized to a common beat. When at least one of the one or more audio clips is discontinued and/or at least one additional audio clip of the audio clips is initiated, the beat may be maintained. The method may facilitate a quick change in the audio clip(s) in response to the sensor signal reaching the first or second threshold.

The several audio clips having a synchronized beat may have identical tempo and may be in phase.

Discontinuing at least one of the one or more audio clips may comprise fading out the at least one of the one or more audio clips.

Initiating at least one additional audio clip of the audio clips may comprise fading in the at least one additional audio clip.

Discontinuing at least one of the one or more audio clips and/or initiating at least one additional audio clip of the audio clips may comprise performing a cross-fade between the at least one of the one or more audio clips and the at least one additional audio clip.

Initiating at least one additional audio clip may comprise determining an offset play position from which the at least one additional audio clip is played.

The offset play position of the at least one additional audio clip may be determined based on a play position of the at least one of the one or more audio clips at the time at which the received sensor signal exceeds the first threshold or falls below the second threshold, or based on a play position of the at least one of the one or more audio clips at the time at which the at least one additional audio clip is initiated.

When the at least one of the one or more audio clips and the at least one additional audio clip have different lengths, the offset play position of the at least one additional audio clip may be determined based on a ratio of a length of the at least one of the one or more audio clips to a length of the at least one additional audio clip. The offset play position may also be determined based on a global count (e.g. a clock or a sample counter), such that the offset play position equals the result of a modulo operation with the global count as numerator and the number of samples in the at least one additional audio clip as denominator. For illustration rather than limitation, the offset play position may be determined as: offset play position=(global sample count) % (number of samples in the at least one additional audio clip).

The one or more audio clips and the at least one additional audio clip may be synchronized to a common beat.

The method may comprise adjusting the common beat based on at least one physiological parameter of a person performing the physical exercise.

Outputting an audio signal may comprise playing the one or more audio clips in a loop until the received sensor signal exceeds the first threshold or falls below the second threshold. Alternatively, the one or more audio clips may be played a pre-determined number of times only, e.g., only once or only n times, with n being an integer greater than one.

Outputting an audio signal may comprise playing the at least one additional audio clip in a loop after the received sensor signal has exceeded the first threshold or has fallen below the second threshold.

The method may further comprise adapting the one or more audio clips or the additional audio clip as a function of an elapsed time since the start of the physical exercise. The method may also comprise adapting the one or more audio clips or the one or more additional audio clips as a function of movement characteristics determined based on the sensor signal. The one or more audio clips or the additional audio clip may be adapted, e.g. exchanged, as a function of the movement characteristics, thereby affording control over the one or more audio clips or the additional audio clip by means of a type of gesture recognition. The gesture recognition may not only be responsive to the position(s) of the person's body parts, but also to the change in position(s), i.e., the movement pattern of the body parts. The movement characteristics can be differentiated with pattern classification algorithms, for example. The method may also comprise adapting the one or more audio clips or the one or more additional audio clips as a function of parameters derived from environmental changes that are unrelated to the movement of the user during the physical exercise. The environmental parameters may include positions and/or position changes of real world objects and/or virtual reality objects. Alternatively or additionally, the method may further comprise adapting the one or more audio clips or the additional audio clip as a function of at least one physiological parameter of a person performing the physical exercise. Heart rate, breathing rate, and a sensed resistance or conductivity of the person's skin are merely exemplary for such physiological parameters that may influence the adaptation of the one or more audio clips or the additional audio clip.

The several audio clips may comprise sampled audio data. Alternatively or additionally, the several audio clips may comprise Musical Instrument Digital Interface (MIDI) clips. Alternatively or additionally, the several audio clips may comprise Open Sound Control (OSC) clips. The several audio clips are not limited to sampled audio data, MIDI clips and/or OSC clips. The several audio clips may include at least one clip having a format other than sampled audio data, a MIDI clip, and an OSC clip, such as a proprietary format.

At least two of the several audio clips may respectively be sub-ranges of an audio file. For illustration rather than limitation, the at least one audio clip that is discontinued may be a first sub-range of the audio file and the at least one additional audio clip that is initiated may be a second sub-range of the audio file. The first and second sub-ranges of the audio file may be different from each other. The first and second sub-ranges of the audio file may be disjoint. Thus, one audio file may be used to derive the several audio clips therefrom.

The sensor may be mounted to an exercise device. The exercise device to which the sensor is mounted may be selected from a group consisting of a stationary bicycle, a running or walking machine, an elliptical machine, a glider machine, a climbing machine, a rowing machine, a skiing machine, free weights, such as dumbbells, kettle bells, or barbells, resistance bands, a weight machine, such as a stack machine, or a plate-loaded machine, and a flexion machine. The sensor may be detachably mounted to the exercise device, so as to facilitate repeated reversible installation and de-installation of the sensor on the exercise device.

The sensor may be configured to capture at least one parameter of a physical exercise without being mounted to an exercise device. The sensor may a wearable sensor. The sensor may be a hand-held sensor or may be integrated in a hand-held device. The sensor may be a multipurpose sensor, operative to sense parameters such as button press and/or voice command in addition to sensing movement during an exercise. Alternatively or additionally, the sensor may be operative to capture at least one kinematic parameter of the user's movement in a contact-free fashion. The sensor may comprise one of a video sensor or an ultrasound sensor to detect the user's movement in a contact-free fashion. The sensor may comprise a camera system having one, two, or more than two cameras. The camera system may be a two-dimensional or three-dimensional camera system. The detected movement may be processed to derive a kinematic parameter, such as a position, velocity, and/or acceleration of at least a part of the user's body. Alternatively or additionally, the detected movement may be processed to determine an overlap of the detected movement with a pre-determined movement pattern.

The method may comprise processing a sensor output of the sensor to generate the sensor signal. The sensor signal may be indicative of a magnitude of the sensor output. Alternatively or additionally, the sensor signal may be indicative of a rate of change of the sensor output (e.g., a rate of direction changes during cyclic physical exercises). The sensor signal may indicate a time derivative of the sensor signal, e.g., to indicate a velocity. The sensor signal may define the on- and offset of the relevant part of the sensor output. This may, for example, be defined through one or more specified tokens (which may be triggered, e.g., by a button press). The sensor may compare the physical movement of the user to one or several pre-determined movement patterns and may provide a sensor signal which is indicative of a similarity of the physical movement of the user with the one or several pre-determined movement patterns. The sensor or a control circuit separate from the sensor may perform the comparison of the physical movement of the user to one or several pre-determined movement patterns using a similarity function. Alternatively or additionally, the sensor or a control circuit separate from the sensor may perform the comparison of the physical movement of the user to one or several movement pattern(s) captured by other sensors and representing movement of other users.

The comparison may be performed in a quantitative manner, using a similarity function. The similarity function may be a metric function or a functional that quantifies the degree of similarity of the physical movement of the user to one or several pre-determined movement patterns. The detected physical movement of the user may be subject to a Fourier transform or other spectral transform, e.g., by using a Fast Fourier Transform (FFT) algorithm, and the transformed data may be input to the similarity function. The similarity function may be a cross-correlation for discrete functions, for example.

By comparing the physical movement of the user to one or several movement pattern(s) of other users and by controlling the acoustic feedback based thereon, group exercise effects may be implemented. For illustration, two or more than two users may be required to move in a coordinated manner in order to cause at least one of the one or more audio clips to be discontinued and/or at least one additional audio clip of the audio clips to be initiated.

The several audio clips having a synchronized beat may exhibit repeated temporal events that relate to identical intervals therebetween or a recurring pattern of maximum acoustic amplitude or timbre events. The temporal events of the several audio clips may be in temporal alignment with a common beat.

The several audio clips having a synchronized beat may exhibit repeated temporal events that relate to identical intervals therebetween or a recurring pattern of maximum acoustic amplitude or timbre events in temporal alignment with a common beat. Initiating at least one additional audio clip may comprise determining an offset play position from which the at least one additional audio clip is played, wherein the offset play position of the at least one additional audio clip is determined based on a play position of the at least one of the one or more audio clips or on a global count at the time at which the received sensor signal exceeds the first threshold or falls below the second threshold or based on a play position of the at least one of the one or more audio clips at the time at which at least one additional audio clip of the audio clips is initiated.

The at least one additional audio clip that is initiated in response to the sensor signal reaching the first threshold may depend on a rate of change of the sensor signal and on a direction in which the first threshold is crossed.

Three or more than three sensor signals may be processed to determine which one of the several audio clips is to be output.

The method may further comprise outputting visual signals. The visual signals may comprise information on the physical exercise that is to be performed and/or on the parts of the body that require further exercise and/or on the way in which the user is to be suspended in an exercise device for the physical exercise. Alternatively or additionally, the visual signals may comprise visual effects. The visual effects may comprise graphical animations. The visual signal may be controlled by the same sensor signal(s) that control the audio feedback.

The physical exercise may be performed on an exercise device or a recreation device that allows a user's orientation in three-dimensional real world space to be controlled to selectively exercise different parts of the user's body. The exercise device or recreation device may be controllable via an input element, such as a joystick, that sets the user's orientation in three-dimensional real world space. The method may comprise outputting visual signals. The visual signals may comprise information on the physical exercise that is to be performed and/or on the parts of the body that require further exercise and/or on the way in which the user is to be suspended in an exercise device for the physical exercise. Alternatively or additionally, the visual signals may comprise visual effects. The visual effects may comprise graphical animations. The visual signal may be controlled by the same sensor signal(s) that control the audio feedback.

The sensor signal may be captured by a sensor that is attachable to an elastic member of an exercise device. The sensor may be releasably attachable to the elastic member, without requiring the elastic member to be modified or disassembled. The elastic member may be an elastic band or elastic rope.

The sensor may be configured to be clipped onto the elastic member. The sensor may comprise a housing on which a bracket is mounted for clipping the sensor onto the elastic member. The bracket may be biased towards the housing for retaining the sensor on the elastic member.

The sensor may be configured to detect a tension and/or compression of the elastic member. Alternatively or additionally, the sensor may be configured to detect an orientation of the elastic member.

The method may further comprise monitoring a sensor output in a calibration routine. A processing routine for processing sensor outputs to generate sensor signals that are then compared with the first and second thresholds may be calibrated based on the sensor signal monitored in the calibration routine. The sensor output monitored in the calibration routine may be used to determine a scaling factor with which a sensor output is multiplied before it is compared to the first and second thresholds. Alternatively or additionally, more complex mapping techniques may be used to process a sensor output to generate the sensor signal therefrom. For illustration, different functions or tables may be used to map a sensor output onto a sensor signal which is then compared to the first and second thresholds. The functions or tables may be adjusted in dependence on the sensor output monitored in the calibration routine. The plurality of audio clips may be selected in dependence on the sensor signal in the calibration routine.

The calibration may be performed so as to provide an improved audio feedback that matches the user's physical exercise in an optimum manner.

The sensor output may be monitored through a minimum number of repetitions of a user's movement in the calibration routine. The minimum number of repetitions may depend on the type of sensor that is used and/or whether the user's movement is a cyclical movement.

Monitoring the sensor output in the calibration routine may comprise determining a start point and an end point of the user's movement while the user's movement is performed at least once in the calibration routine.

When the sensor is configured to detect free movements in space, as may be the case for a 3D camera system, for example, the calibration routine may comprise monitoring the sensor output through at least two repetitions of the user's movement.

When the physical exercise is a physical exercise that involves a cyclical movement pattern, as may be the case for running or cycling, a different calibration routine may be used. For illustration, a height to which the user lifts his/her legs when running, a frequency at which the user lifts his/her legs when running, and/or a pedaling frequency when cycling may be monitored in the calibration routine. The acceleration may additionally be monitored. The sensor output may be processed to obtain various values, e.g., activity values.

The first and second thresholds may be adjusted while a calibrated movement is carried out, i.e., after calibration. This allows an adaptation to be performed for specific exercises or for specific exercise devices.

One, at least two, or all of the several audio clips may be provided by a sequencer. Alternatively or additionally, the audio signal or data relating to the audio signal may be provided to the sequencer. The sequencer may be implemented by hardware or software.

The sequencer may provide one or several data streams that can be used to control the audio feedback system.

A device for controlling acoustic feedback during a physical exercise according to the invention comprises:
 a memory storing several audio clips having a synchronized beat;
 an input to receive a sensor signal having a sensor signal range divided by first and second thresholds into at least three sensor signal sub-ranges; and
 a control circuit to control outputting of an audio signal in response to the received sensor signal, the output audio signal comprising one or more of the audio clips output in a synchronized manner.

The control circuit is configured to cause at least one of the one or more audio clips to be discontinued and/or at least one additional audio clip of the audio clips to be initiated in synchronization with the one or more audio clips if the received sensor signal exceeds the first threshold. The control circuit is configured to cause at least one of the one or more audio clips to be discontinued and/or at least one additional audio clip of the audio clips to be initiated in synchronization with the one or more audio clips if the received sensor signal falls below the second threshold.

The several audio clips having a synchronized beat may have identical tempo and may be in phase.

The device may further comprise an electroacoustic transducer to output the audio signal. The electroacoustic transducer may comprise a loudspeaker, an ear speaker, a head phone, or another electroacoustic transducer.

The device may be configured to receive a plurality of sensor signals, each from an associated one of a plurality of sensors. The device may be configured to control outputting of a plurality of audio signals, each of which is respectively associated with at least one of the sensor signals, as a function of the respective associated sensor signal.

The device may be configured to output visual signals. The visual signals may comprise information on the physical exercise that is to be performed and/or on the parts of the body that require further exercise and/or on the way in which the user is to be suspended in an exercise device for the physical exercise. Alternatively or additionally, the visual signals may comprise visual effects. The visual effects may comprise graphical animations. The visual signal may be controlled by the same sensor signal(s) that control the audio feedback.

The sensor may be attachable to an elastic member of an exercise device. The sensor may be releasably attachable to the elastic member, without requiring the elastic member to be modified or disassembled.

The sensor may be configured to be clipped onto the elastic member. The sensor may comprise a housing on which a bracket is mounted for clipping the sensor onto the elastic member. The bracket may be biased towards the housing for retaining the sensor on the elastic member.

The sensor may be configured to detect a tension and/or compression of the elastic member. Alternatively or additionally, the sensor may be configured to detect an orientation of the elastic member.

The control circuit may be configured to perform the method of any one of the embodiments disclosed herein.

A system according to an embodiment comprises a sensor responsive to a person's actions during a physical exercise and the device of any one of the embodiments disclosed herein. The sensor may provide an output signal having a signal sensor range.

The system may further comprise an exercise device, with the sensor being mounted to the exercise device. As mentioned above, the exercise device to which the sensor is mounted may be selected from a group consisting of a stationary bicycle, a running or walking machine, an elliptical machine, a glider machine, a climbing machine, a rowing machine, a skiing machine, free weights, such as dumbbells, kettle bells, or barbells, resistance bands, a weight machine, such as a stack machine, or a plate-loaded machine, and a flexion machine.

The exercise device or recreational device may allow a user's orientation in three-dimensional real world space to be controlled to selectively exercise different parts of the user's body. The exercise device or recreational device may be controllable via an input element, such as a joystick, that sets the user's orientation in three-dimensional real world space. Alternatively or additionally, the exercise device or recreational device may be configured to automatically transition through a sequence of orientations and/or movements in three-dimensional real world space. The exercise device or recreational device may be configured to suspend the user, e.g., by supporting the user on or along the user's hip, such that the user's orientation in three-dimensional real world space can be controlled.

Responsive to the user's orientation in three-dimensional real world space or other sensor signals, the device for outputting audio information may additionally provide visual signals. The visual signals may comprise information on the physical exercise that is to be performed and/or on the parts of the body that require further exercise and/or on the way in which the user is to be suspended in an exercise device for the physical exercise. Alternatively or additionally, the visual signals may comprise visual effects. The visual effects may comprise graphical animations. The visual signal may be controlled by the same sensor signal(s) that control the audio feedback.

One particularly preferred exercise device comprises two objects which are connected to one another by an elastic element. These objects may be grips, balls, batons, barbells or any other kind of objects which may easily be gripped by or held within a user's hand. The elastic element may, e.g., be an elastic band or rope. The elastic band or rope may have a length in its relaxed state of between 10 cm and 1 m, preferably of between 20 cm and 60 cm. When subject to admissible loads, the length of the elastic element may change by less than 30 cm, preferably by less than 20 cm, even more preferably by less than 10 cm. Preferably, the elastic element can be stretched to at least twice of its relaxed length applying a stretching force in the range between 20 N and 200 N, preferably between 40 N and 100 N. The sensor in this case preferably comprises an accelerometer and/or a gyrometer and/or a strain gauge and/or a load cell mounted on or within at least one of the two objects and/or on or within the elastic element. Alternatively, the elastic element could be the sensor. Preferably, each of the objects to which the elastic element is mounted comprises a sensor. Utilizing the sensor mounted to one or both of the objects or the elastic element, or using the elastic element as a sensor, several parameters can be used as the sensor output of the present invention. For example, the sensor signal may be associated with the extension of the elastic element, i.e. the force applied to the elastic element. The sensor signal may comprise plural data items, thereby representing a vector in a multi-dimensional sensor signal space. The plural data items may comprise at least two pieces of data selected from a group consisting of position, velocity, acceleration, coordinate axis, movement direction, and force. In addition, or alternatively, the sensor signal may be related to the velocity of moving one or both of the objects, or the velocity of the expansion of the elastic element, and/or the direction in which the objects are being moved, and/or the direction in which the elastic element is being expanded.

This allows for a particularly versatile use of this exercise device, wherein different sounds may be generated if the two objects, or the elastic element, is or are, e.g., moved or stretched within a horizontal plane or within a vertical plane. With a multitude of different sounds (or clips) being allocated to various different movements of the two objects, or to the elastic element, this particular exercise device may be "played" like an instrument which has been shown to be particularly motivating for persons exercising with such a device.

The sensor may be configured to capture at least one parameter of a physical exercise without being mounted to an exercise device. The sensor may comprise a wearable sensor. The sensor may be a hand-held sensor or may be integrated in a hand-held device. Alternatively or additionally, the sensor may be operative to capture the user's movement in a contact-free fashion. The sensor may comprise one of a video sensor or an ultrasound sensor to detect the user's movement in a contact-free fashion. The sensor may comprise a two- or three-dimensional camera system.

The sensor may be configured to compare the physical movement of the user to one or several pre-determined movement patterns and may provide a sensor signal which is indicative of a similarity of the physical movement of the user with the one or several pre-determined movement patterns.

A computer program according to an embodiment comprises software code adapted to perform the method according to any one of the embodiments disclosed herein when executed by a processor.

The method, device, and computer program for controlling acoustic feedback during a physical exercise enable the user to explore a large space of possible sounds and combinations of sounds during an exercise. The method, device, and computer program for controlling acoustic feedback during a physical exercise enable the user to generate acoustic feedback that is considered to be motivating, even when the user has not yet gathered extensive experience with using the acoustic feedback mechanism.

The method, device, and computer program for controlling acoustic feedback according to at least some embodiments allow the audio output to be switched between different audio clips, while respecting the play position and beat of the clip that is discontinued. An additional audio clip may be initiated, e.g., by means of cross-fading, starting at a play position that depends on the play position of the audio clip that is discontinued. With the plural audio clips being in synchronization, i.e., having a common beat, a smooth transition between different clips is attained without requiring the user to synchronize the physical exercise to the beat of the several audio clips.

The method, device, and computer program for controlling acoustic feedback according to at least some embodiments allow the audio output to be generated not only in dependence on a magnitude of a sensor output, but also in dependence on a rate and/or direction of change of the sensor output.

The method, device, and computer program for controlling acoustic feedback may be used to simultaneously generate acoustic feedback for a plurality of exercising people, thus being suitable for use in a group exercise setting, without being limited thereto.

BRIEF DESCRIPTION OF THE DRAWINGS

Preferred embodiments of the present invention will be more fully understood and appreciated by reading the following detailed description in conjunction with the accompanying drawings, in which.

DETAILED DESCRIPTION OF EMBODIMENTS

Figure 1:
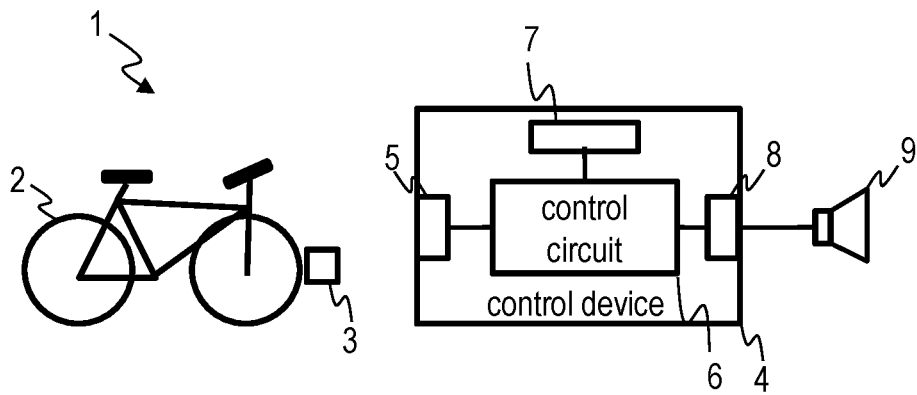
FIG. 1 is a schematic diagram of a system comprising a device for controlling acoustic feedback during a physical exercise according to a preferred embodiment.

Exemplary embodiments of the invention will be described with reference to the drawings in which identical or similar reference signs designate identical or similar elements. Any coupling or connection between functional or structural elements shown in the drawings and/or explained herein may be implemented as a direct or indirect connection, using a physical connection or wireless signal transmission techniques.

While exemplary embodiments will be explained with reference to exercise devices, such as a stationary bicycle, a running or walking machine, an elliptical machine, a glider machine, a climbing machine, a rowing machine, a skiing machine, free weights, such as dumbbells, kettle bells, or barbells, resistance bands, a weight machine, such as a stack machine, or a plate-loaded machine, and a flexion machine, embodiments of the invention are not limited to this exemplary use. Rather, methods, devices, systems, and computer programs according to preferred embodiments may be used to provide acoustic feedback to a user during a physical exercise based on a sensor signal provided by a sensor which may, but does not need to be mounted on an exercise apparatus. Embodiments of the invention may in particular be used to generate audio output in response to a physical exercise that is non-cyclic or that involves non-cyclic movements. In still other embodiments, audio output may be controlled in response to a sensor signal of a sensor installed in a seat, such as a vehicle seat, an office seat, or a residential seat.

According to preferred embodiments of the invention, audio output is controlled in response to a sensor signal. The sensor signal may be the output signal of a sensor that senses movement of a user or of an exercise apparatus. Alternatively, the sensor signal may be derived from the output signal of the sensor by further processing, such as by deriving a velocity from the output signal from a position sensor. The audio clip(s) output during the physical exercise may be selected based on at least one kinematic parameter, such as a position, velocity, and/or acceleration of a part of the user's body or a part of an exercise device during the physical exercise. Both the amplitude and the direction of the movement may be taken into account in the process of selecting the audio clip(s) that is or are to be output.

According to preferred embodiments of the invention, the audio signal may be provided during a physical exercise. The term "physical exercise" may encompass physical activities that may be performed to exercise parts of the user's body. The physical exercise may be performed in dedicated physical exercise environment or may be integrated with other user activities during, e.g., recreational or work activities. The work activities may comprise a user's movement while seated on a chair or other seating furniture, household work, or other work activities. The recreational activities may comprise activities that involve riding fairground rides such as rollercoasters.

According to preferred embodiments of the invention, audio clip(s) that are being output are changed in response to the sensor signal. The change in audio clip(s) can have various forms, including, without limitation:

exchanging a first audio clip by a second audio clip when the sensor signal reaches a threshold; and/or initiating the outputting of a second audio clip in addition to the first audio clip when the sensor signal reaches a threshold.

The change of the audio clip(s) may comprise fading-in at least one audio clip, fading-out at least one additional audio clip, or cross-fading between audio-clips.

The audio clips may have identical tempo and may be in phase.

The one or more additional audio clips that are initiated in response to the sensor signal reaching a threshold may depend on a rate of change of the sensor signal changes and/or on a direction in which the threshold is crossed. For illustration, different additional audio clip(s) may be initiated depending on the rate of change of the sensor signal when the threshold is reached and/or depending on whether the sensor signal exceeds or falls below the threshold.

The audio clip(s) that is or are discontinued and the additional audio clip(s) that is or are initiated in response to the sensor signal reaching a threshold may have a synchronized beat. A beat of the discontinued audio clip(s) and a beat the additional audio clip(s) may be aligned in time. Both the beat of the discontinued audio clip(s) and the beat the initiated additional audio clip(s) may be synchronized with a common beat, e.g., such that amplitudes in the acoustic volume of the discontinued audio clip(s) and amplitudes in acoustic volume of the initiated additional audio clip(s) respectively have a recurring time pattern that is in temporal alignment with the common beat.

The change in audio clip(s) may respect the play position at the time at which the change in audio clip(s) occurs. For illustration, if a first audio clip is output prior to the sensor signal reaching the threshold and a second audio clip is initiated in response to the sensor signal reaching the threshold, an offset play position (also referred to as playhead offset herein) from which the second audio clip is output may depend on the play position of the first audio clip at the time at which the second audio clip is initiated.

The audio clip(s) may be played in a loop, until an event occurs. The event may comprise the sensor signal reaching a threshold, triggering a change in audio clip(s). The event may comprise a detection of a specific movement pattern in the sensor signal, as determined by pattern classification. The event may comprise expiry of a predefined time period, causing audio clip(s) to be exchanged as a function of time even when the sensor signal does not reach any one of the thresholds. Alternatively or additionally, thresholds defining the boundaries of sensor sub-ranges may be varied as a function of time or in dependence on events detected by the sensor. The event may comprise the recognition of a movement pattern with pattern classification algorithms or other events derived from environmental changes that are unrelated to the movement of the user during the physical exercise. The environmental changes may include changes in position of real world objects and/or virtual reality objects, for example.

The loop length may be variable. The loop length may be altered as a function of the sensor signal, as a function of the time period for which the physical exercise has been performed, or as a function of other parameters, such as environmental conditions unrelated to the physical exercise.

The above and additional features of exemplary embodiments described in more detail below enable the audio output to be rapidly switched between different audio clips. The immediate and for the user predictable change between audio clips at specific sensor input values allows the user to explore different sounds as a function and under the control of his or her body movements. The user is enabled to generate a wide variety of different sounds, without requiring the user's movements to be coordinated with a beat of the acoustic output. The methods and systems allow the user to generate acoustic output that is considered to be motivating without requiring the user to spend an extended time period learning how to operate the system.

FIG. 1 is a schematic diagram of a system which comprises a control device for controlling acoustic feedback according to a preferred embodiment. The system generally comprises a sensor, the control device, and an electroacoustic transducer. The control device may comprise a portable or stationary computing device. The control device is operative to control the outputting of audio clip(s) in dependence on a sensor signal that is based on a sensor output of the sensor.

The sensor may be mounted to an exercise device. The exercise device may be a stationary exercise device, such as, without limitation, a stationary bicycle, a running or walking machine, an elliptical machine, a glider machine, a climbing machine, a rowing machine, a skiing machine, free weights, such as dumbbells, kettle bells, or barbells, resistance bands, a weight machine, such as a stack machine, or a plate-loaded machine, and a flexion machine. The exercise device may allow the user to perform a physical exercise that is non-cyclic or that involves non-cyclic movements.

The sensor does not need to be coupled to an exercise device. For illustration, the sensor may be a wearable sensor, such as an acceleration sensor mounted in a wrist-strap or other wearable device, to capture movements of the user. Alternatively or additionally, the sensor may be configured to capture kinematic parameters of the user's movements without requiring direct attachment to the user's body or an exercise device. The sensor may comprise an optical image sensor to capture the user's movements using image processing techniques, or the sensor 3 may comprise an ultrasound sensor or other distance-sensing sensor to capture the user's movements. The sensor may comprise one or several two- or three-dimensional cameras. Video frames captured by the two- or three-dimensional cameras may be evaluated by the control device to derive a movement pattern. Transitions between audio clip(s) may be controlled based on the movement pattern.

The control device may comprise an input interface for unidirectional or bidirectional communication with the sensor. The input interface may be configured to receive the sensor output from the sensor. The control device may comprise a control circuit. The control circuit may comprise one or several integrated circuits. The control circuit 6 may comprise one or several of an application specific integrated circuit (ASIC), a controller, a microcontroller, a processor, a microprocessor, or any combination thereof.

As will be explained in more detail below, the control circuit is operative to determine which audio clip(s) is or are to be output and to provide audio samples for outputting via an output interface. The output interface may comprise a digital-to-analog converter (DAC). The control circuit may be operative to exchange audio clip(s) in response to the sensor signal reaching first and second thresholds. The change in audio clip(s) may preserve the play position, causing at least one additional audio clip to be initiated from an offset play position that depends on a play position of the audio clip(s) that were output prior to the sensor signal reaching the threshold.

The control device may comprise a memory or storage device for storing several audio clips. Not all possible audio clips that can be played back need to be stored locally in the control device. At least some of the several audio clips may be retrieved via a local area network or wide area network from a data repository. Retrieval of audio clips may be performed as it is required during operation of the control device. For illustration, for a long exercise session, additional audio clips may be downloaded to ensure that new audio output can continue to be generated.

The several audio clips stored in memory may respectively be synchronized. The several audio clips may have a synchronized beat. As used herein, the term beat refers to the basic time unit or pulse in an audio clip, which may be reflected by repeated temporal events that are related to recurring identical intervals when the audio clip is output.

The several audio clips stored in memory may have identical tempo and may be in phase.

The system comprises an electroacoustic transducer, which may be a loudspeaker, ear speaker, head phone, or other device capable of converting electric signals into audible sound. The electroacoustic transducer may be integrated into a common housing with the control device or may be provided separately from the control device.

A method that may be automatically performed by the control device will be explained in more detail below.

Figure 2:
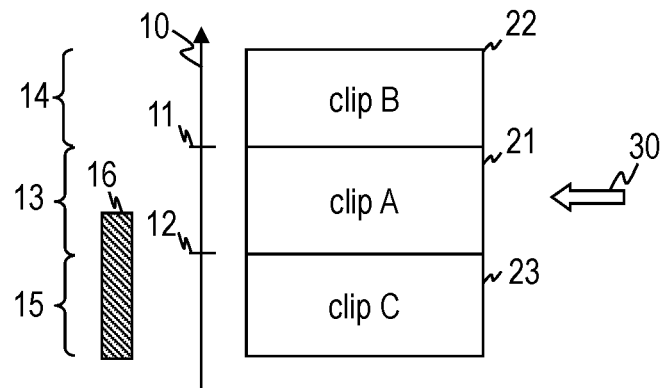
FIG. 2, FIG. 3, and FIG. 4 are diagrams illustrating operation of the device according to a preferred embodiment.
Figure 3:
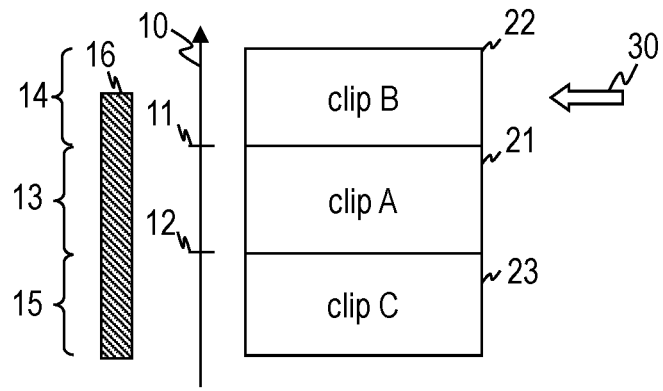
Figure 4:
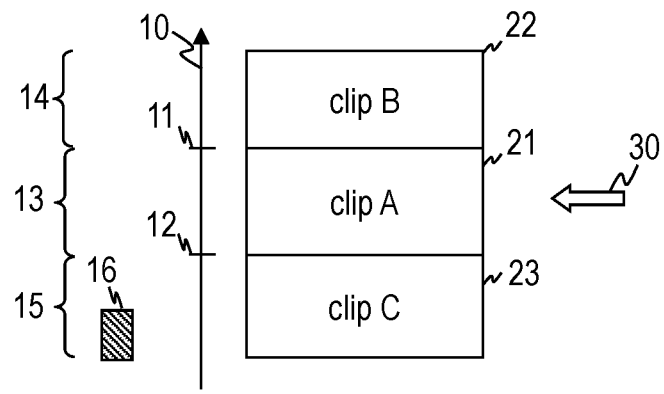

FIG. 2, FIG. 3, and FIG. 4 are diagrams illustrating the provision of acoustic feedback during a physical exercise. A sensor signal range is subdivided by a first threshold and a second threshold into a plurality of sensor signal sub-ranges. For illustration, a first sensor signal sub-range may extend between the second threshold and the first threshold. A second sensor signal sub-range may comprise sensor signal values that exceed the first threshold. A third sensor signal sub-range may comprise sensor signal values that are less than the second threshold. While not depicted in FIG. 2, each one of the sub-ranges may respectively be defined by a lower and upper threshold that define the boundaries of the respective sub-range.

When the sensor signal has a value within the first sensor signal sub-range, at least one audio clip is output. The at least one audio clip may be associated with the first sensor signal sub-range. The control device may select the at least one audio clip for outputting when the sensor signal is within the first sensor signal sub-range, as schematically indicated by a selection arrow.

As illustrated in FIG. 3, when the sensor signal increases so as to exceed the first threshold, outputting of the at least one additional audio clip may be initiated. The at least one additional audio clip may be associated with the second sensor signal sub-range. Alternatively or additionally, outputting of the at least one audio clip associated with the first sensor signal sub-range may be discontinued. Discontinuing the at least one audio clip may comprise fading out the at least one audio clip. Initiating the at least one additional audio clip may comprise fading in the at least one additional audio clip. The change in audio output may comprise performing a cross-fade from the at least one audio clip to the at least one additional audio clip. The cross-fade may be completed within a time of less than 1 second, preferably of less than 0.5 seconds, after the sensor signal has exceeded the first threshold. The cross-fade may be performed in such a manner that cross-fading does not lead to abrupt changes in magnitude of an acoustic signal output by the electroacoustic transducer. The control device may be operative to adjust the digital audio signal by adjusting gain settings, for example, in such a manner that the cross-fade does not lead to abrupt changes in magnitude of the acoustic signal output by the electroacoustic transducer.

As illustrated in FIG. 4, when the sensor signal decreases so as to fall below the second threshold, outputting of at least one additional audio clip may be initiated. Alternatively or additionally, outputting of the at least one audio clip associated with the first sensor signal sub-range may be discontinued. The at least one additional audio clip may be associated with the third sensor signal sub-range. Discontinuing the at least one audio clip may comprise fading out the at least one audio clip. Initiating the at least one additional audio clip may comprise fading in the at least one additional audio clip. The change in audio clip may comprise performing a cross-fade from the at least one audio clip to the at least one additional audio clip. The cross-fade may be completed within a time of less than 1 second, preferably of less than 0.5 seconds, after the sensor signal has exceeded the first threshold. The cross-fading may be performed in such a manner that the cross-fading does not lead to abrupt changes in acoustic magnitude output by the electroacoustic transducer. The control device may be operative to adjust the digital audio signal by adjusting gain settings, for example, in such a manner that the cross-fade does not lead to abrupt changes in magnitude of the acoustic signal output by the electroacoustic transducer.

More than one audio clip may respectively be associated with at least one sensor signal sub-range. For illustration, a plurality of additional audio clips may be associated with the second sensor signal sub-range. The additional audio clip(s), which is or are output when the sensor signal exceeds the first threshold, may be selected based on a velocity of the user's movements during an exercise, which may be reflected by a rate of change of the sensor output. Alternatively or additionally, the additional audio clip(s) output when the sensor signal exceeds the first threshold may be selected based on time for which the exercise has been ongoing. This allows the at least one additional audio clip, which is initiated in response to the sensor signal exceeding the first threshold, to be varied as a function of the duration of a physical exercise.

Alternatively or additionally, the additional audio clip(s) output when the sensor signal exceeds the first threshold may be selected based on the recognition of a movement pattern with pattern classification algorithms or other events derived from environmental changes that are unrelated to the movement of the user during the physical exercise.

Alternatively or additionally, a plurality of additional audio clips may be associated with the second sensor signal sub-range. The additional audio clip(s), which is or are output when the sensor signal falls below the second threshold, may be selected based on a velocity of the user's movements during an exercise, which may be reflected by a rate of change of the sensor output. Alternatively or additionally, the additional audio clip(s), which is or are output when the sensor signal falls below the second threshold, may be selected based on time for which the exercise has been ongoing. This allows the at least one additional audio clip, which is initiated in response to the sensor signal falling below the second threshold, to be varied as a function of the duration of a physical exercise.

Alternatively or additionally, the additional audio clip(s) output when the sensor signal falls below the second threshold may be selected based on the recognition of a movement pattern with pattern classification algorithms or other events derived from environmental changes that are unrelated to the movement of the user during the physical exercise.

The audio clip and the at least one additional audio clip have a synchronized beat. The audio clip and the at least one additional audio clip may be synchronized to a common beat. The audio clip and the at least one additional audio clip may respectively have a beat that may be reflected by repeated temporal events that relate to identical intervals therebetween or a recurring pattern of maximum acoustic amplitude or timbre event, that is in temporal alignment with the common beat.

As will be explained in more detail below, the change in audio clip that is triggered by the sensor signal exceeding the first threshold or falling below the second threshold may respect the play position, thereby automatically maintaining the beat when at least one audio clip is discontinued and/or at least one additional audio clip is initiated. In some preferred embodiments, an offset play position from which rendering of the at least one additional audio clip is started may depend on the play position of the at least one audio clip at that point in time at which the at least one additional audio clip is initiated, or on a global count (e.g. a clock or a sample counter), such that the offset play position may be determined to be equal to the result of a modulo operation with the global count as numerator and the number of samples in the audio clip as denominator. For illustration, the play offset may be determined as (global sample count) % (number of samples in the at least one additional audio clip), as will be explained in more detail with reference to FIG. 7 to FIG. 11 below.

Figure 5:
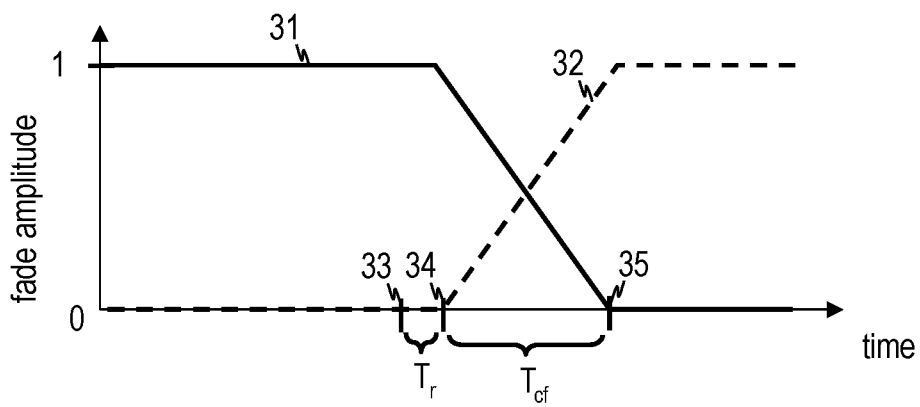
FIG. 5 is a diagram illustrating exemplary weighting functions for fading in and fading out audio clips in response to a sensor signal during the physical exercise.
Figure 6:
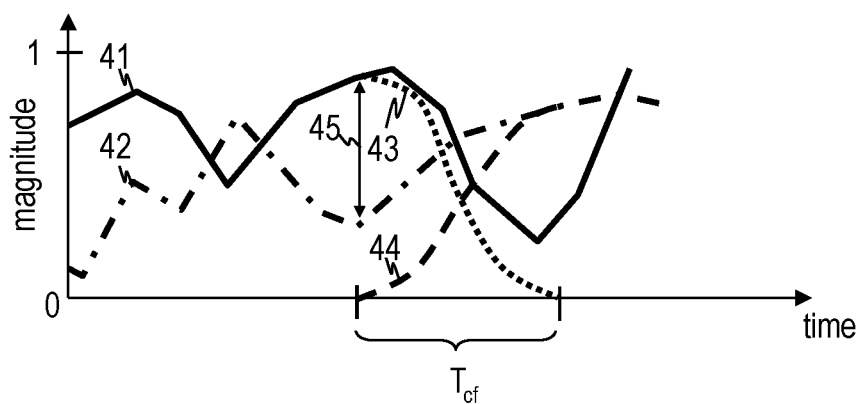
FIG. 6 is a diagram illustrating an exemplary change in audio amplitude during a cross-fade performed during a physical exercise.

FIG. 5 and FIG. 6 illustrate a cross-fading that may be performed when the at least one audio clip is discontinued and the at least one additional audio clip is initiated. FIG. 5 shows fade amplitudes applied to the audio clips at least during a cross-fade time period $T_{cf}$. A fade amplitude may be applied to the sound amplitude of the at least one audio clip that is discontinued in response to the sensor signal leaving the first sensor signal sub-range. Another fade amplitude may be applied to the at least one additional audio clip that is initiated in response to the sensor signal entering the second or third sensor signal sub-range respectively. The sensor signal may reach the first or the second threshold at time. The cross-fade is initiated with a slight time delay $T_r$ at time. The time delay $T_r$ may correspond to the response time of the sensor and of the control device. The time delay $T_r$ may be less than 1 second, preferably less than 0.5 seconds, even more preferably less than 0.3 seconds. In a cross-fade period $T_{cf}$ between time 34 and time 35, the amplitude of the at least one audio clip, which is discontinued, may be gradually reduced. The amplitude of the at least one additional audio clip which is initiated, may be gradually increased. The decrease and increase in amplitude, respectively, may be obtained using a multiplicative factor for the sound amplitude that is schematically illustrated by the fade amplitudes. The fade amplitude may be a monotonously decreasing function. The fade amplitude may be a monotonously decreasing function. The fade amplitude may be a linear function. The fade amplitude may be a non-linear function, such as a logarithmic, exponential, trigonometric, sine-type, arc tangent, or similar function. Such non-linear functions mitigate the risk of significant magnitude changes. The fade amplitude may be a monotonously increasing function. The fade amplitude may be a linear function. The fade amplitude may be a non-linear function, such as a logarithmic, exponential, trigonometric, arc tangent, or similar function. Such non-linear functions mitigate the risk of significant magnitude changes. The fade amplitudes may be applied to a gain setting, for example, that defines the maximum acoustic magnitude.

FIG. 6 illustrates the effect of the cross-fading. An acoustic magnitude of the at least one audio clip that is discontinued is schematically illustrated by a solid line. An acoustic amplitude of the at least one additional audio clip that is initiated is schematically illustrated by dashed-dotted line. At the beginning of the cross-fading, the at least one audio clip and the at least one additional audio clip may exhibit a difference in magnitude. In order to prevent sudden and abrupt changes in audio output magnitude, which could give rise to undesirable click noises, a monotonously decreasing fade amplitude may be applied to the at least one audio clip, causing the output amplitude of the at least one audio clip to gradually decrease, as illustrated by dotted line. A monotonously increasing fade amplitude may be applied to the at least one additional audio clip causing the output amplitude of the at least one additional audio clip to gradually increase, as illustrated by dashed line. The overall sound magnitude that results from the combination of the at least one audio clip, with the monotonously decreasing fade amplitude applied thereto, and of the at least one additional audio clip with the monotonously increasing fade amplitude applied thereto, does not exhibit pronounced abrupt changes in the output overall acoustic volume.

The change from the at least one audio clip to the at least one additional audio clip may be performed in such a manner that the play position is preserved, thereby ensuring that the at least one additional audio clip is initiated in synchrony with the at least one audio clip that was already output prior to the sensor signal reaching the threshold. More specifically, according to preferred embodiments, the at least one additional audio clip is initiated to play from an offset play position that is determined as a function of the play position of the at least one audio clip at the time at which the at least one additional audio clip is initiated, or on a global count (e.g. a clock or a sample counter), such that the offset play position may be determined to be equal to the result of a modulo operation with the global count as numerator and the number of samples in the audio clip as denominator. For illustration, the play offset may be determined as (global sample count) % (number of samples in the at least one additional audio clip), as will be explained in more detail with reference to FIG. 7 to FIG. 11.

Figure 7:
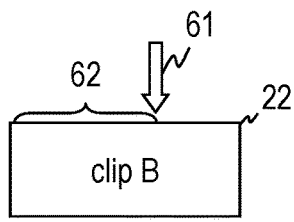
FIG. 7 is a diagram illustrating the determination of an offset play position in response to a sensor signal during a physical exercise.

FIG. 7 illustrates the at least one additional audio clip that is initiated in response to the sensor signal reaching first threshold. An offset play position 61 from which the at least one additional audio clip is initiated may, but does not need to correspond to the beginning of the at least one additional audio clip. More specifically, the offset play position from which the at least one additional audio clip is played may depend on the play position of the at least one audio clip at the time at which the at least one additional audio clip is initiated. The control device may automatically determine a playhead offset for the play position of the at least one additional audio clip. When initiating the at least one additional audio clip, audio data within the playhead offset are not output until after the end of the at least one additional audio clip has been played for the first time. The at least one additional audio clip may optionally be played in a loop. It will be appreciated that, after the end of the at least one additional audio clip has been reached for the first time, the full length of the at least one additional audio clip may be played in the next loop, causing the audio data in the playhead offset to be also output.

Figure 8:
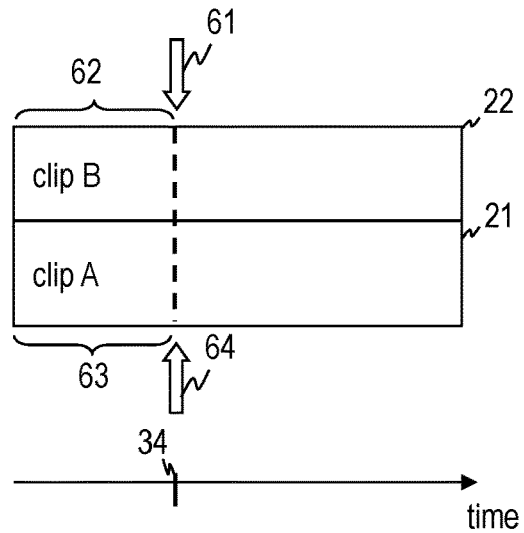
FIG. 8 is a diagram illustrating the determination of an offset play position in response to a sensor signal during a physical exercise.

FIG. 8 illustrates the at least one audio clip and the at least one additional audio clip that is initiated in response to the sensor signal reaching a threshold. When cross-fading is started at time, the at least one audio clip has a play position. A portion of the at least one audio clip, e.g., a certain number of digital signal processing (DSP) blocks of the at least one audio clip, has already been output when cross-fading is started at the time. When cross-fading is started at time, the at least one additional audio clip is played from the play position at that is determined based on the play position 64 of the at least one audio clip at the start of the cross-fading. When the at least one audio clip and the at least one additional audio clip have identical overall length, the offset play position from which the at least one additional audio clip is played back may be identical to the play position of the at least one audio clip at the time at which the at least one additional audio clip is initiated.

Figure 9:
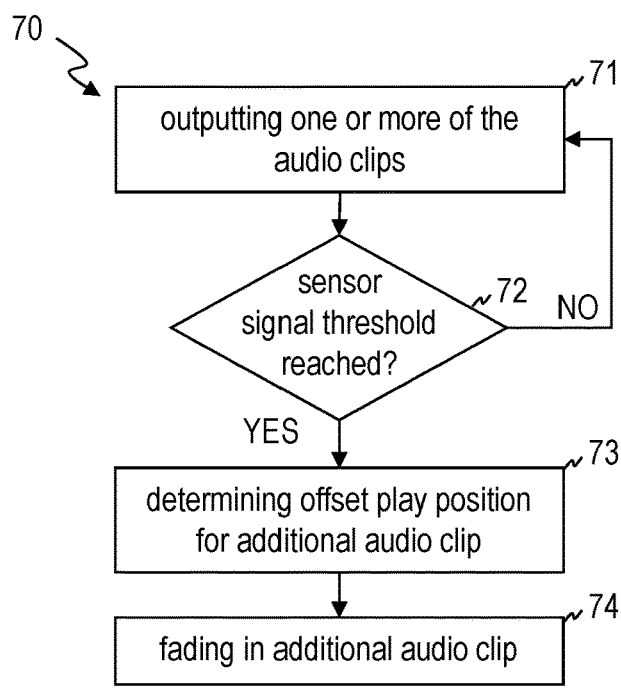
FIG. 9 is a flow chart of a method according to a preferred embodiment.

FIG. 9 is a flow chart of a method according to a preferred embodiment. The method may be performed automatically by the control device. At step 71, one or more of the several audio clips are output. Outputting one or more of the several audio clips may comprise playing the at least one audio clip in a loop until an event occurs. The event may be the sensor signal reaching a threshold, which may cause the at least one audio clip to be discontinued and/or which may cause at least one additional audio clip 22, 23 to be initiated. At step 72, it is determined whether the sensor signal has reached a threshold 11, 12, e.g., whether the sensor signal exceeded a first threshold 11 or has fallen below the second threshold 12. If the sensor signal has not reached the threshold 11, 12, the method returns to step 71 and may continue playing the audio clip 21. The determination at step 72 may be performed for example once per DSP block of the audio clip 21. The determination step 72 may comprise querying the sensor 3 or reading the sensor output at the interface 5. If it is determined that the sensor signal has reached the threshold, in step 73 an offset play position for the at least one additional audio clip 22, 23 is determined. The offset play position may be determined based on the play position of the at least one audio clip 21, or alternatively based on a global count at the time at which the at least one additional audio clip 22, 23 is initiated. At step 74, the at least one additional audio clip 22, 23 is initiated. Initiating the at least one additional audio clip 22, 23 may comprise fading in the at least one additional audio clip 22, 23. Optionally, the at least one audio clip 21 may be concurrently discontinued, e.g., by fading out the at least one audio clip 21 or by cross-fading between the at least one audio clip 21 and the at least one additional audio clip 22, 23.

While the event triggering the transition at step 72 may be a sensor signal reaching a threshold, other and more complex trigger events may be defined. For illustration, two or more users may be required to move in a coordinated manner in order to trigger a transition between audio clips.

The offset play position of the at least one additional audio clip 22, 23 may not only depend on the play position of the at least one audio clip 21, but may also depend on a difference in overall lengths of the audio clip 21 and the additional audio clip 22.

The offset play position of the at least one additional audio clip 22, 23 may be determined based on a global count. The global count may be a clock or a sample counter. The offset play position 61 may be equal to the result of a modulo operation with the global count as numerator and the number of samples in the at least one additional audio clip 22, 23 as denominator, as will be explained in more detail with reference to FIG. 11.

Figure 10:
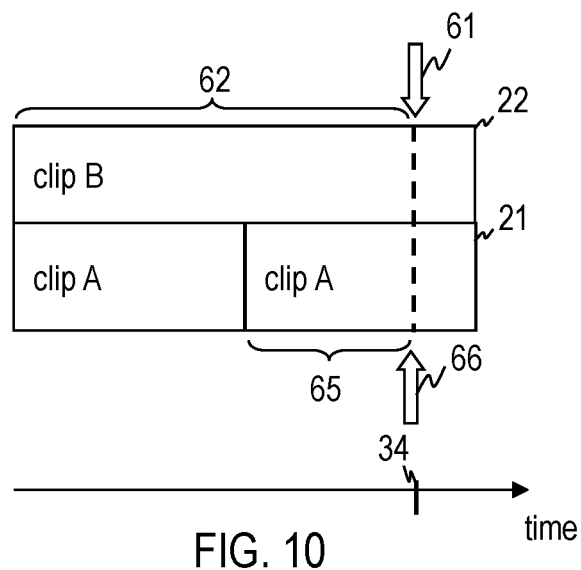
FIG. 10 is a diagram illustrating the determination of an offset play position in response to a sensor signal during a physical exercise.

FIG. 10 illustrates the determination of the offset play position 61 of the at least one additional audio clip 22 when the at least one audio clip 21 and the at least one additional audio clip 22 have different lengths. FIG. 10 schematically illustrates the case that the at least one audio clip 21 has a shorter length than the at least one additional audio clip 22. In this case, the at least one audio clip 21 may already have looped once or several times at the time 34 at which cross-fading is started. The play position 61 of the at least one additional audio clip 22 may be determined to respect the different audio clip lengths. For illustration, the play position 61 may be determined to correspond to the overall length of the at least one audio clip 21 plus the play position 66 of the at least one audio clip 21 at time 34. The play position 66 corresponds to an elapsed time 65 from the beginning of the latest loop of the at least one audio clip 21.

Generally, when the at least one audio clip 21 and the at least one additional audio clip 22 have different lengths, the play position from which the at least one additional audio clip is initiated may depend not only on the play position of the at least one audio clip 21, but also on the ratio of overall lengths of both the at least one audio clip 21 and the at least one additional audio clip 22.

Figure 11:
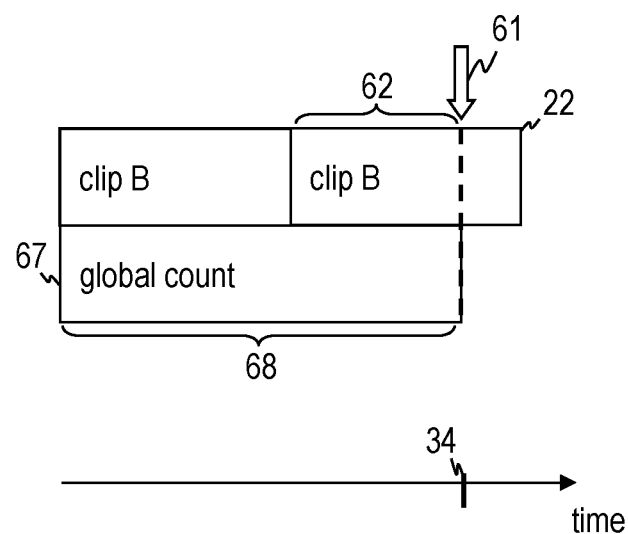
FIG. 11 is a diagram illustrating the determination of an offset play position in response to a sensor signal during a physical exercise.

FIG. 11 illustrates the determination of the offset play position 61 of the at least one additional audio clip 22 based on a global count 67. The global 67 may be a clock or a sample counter. As used herein, the term "global count" refers to a number that increases as time passes and/or as samples are being output. The global count is a global measure of the total amount of time and/or the total number of samples that have been output, irrespective of which audio clip(s) have been output.

The offset play position 61 from which the at least one additional audio clip 22 is initiated may be determined based on the value 68 of the global count 67 at the time 34 at which the at least one additional audio clip 22 is initiated. The offset play position 61 may be equal to the result of a modulo operation with the global count as numerator and the number of samples in the at least one additional audio clip 22 as denominator. For illustration rather than limitation, the offset play position 61 may be determined as: offset play position= (global sample count) % (number of samples in the at least one additional audio clip 22).

In any one of the various preferred embodiments described herein, the association between audio clips and sensor signal sub-ranges may, but does not need to be static. For illustration, different audio clips may be assigned to at least one of the sensor signal sub-ranges, respectively as a function of time from the start of the exercise. In this manner, the risk of the audio feedback becoming monotonous during an exercise may be further reduced. Alternatively or additionally, different audio clips may be assigned to at least one of the sensor signal sub-ranges in response to the recognition of a movement pattern with pattern classification algorithms or other events derived from environmental changes that are unrelated to the movement of the user during the physical exercise. The environmental changes may relate to real world objects and/or virtual reality objects.

Figure 12:
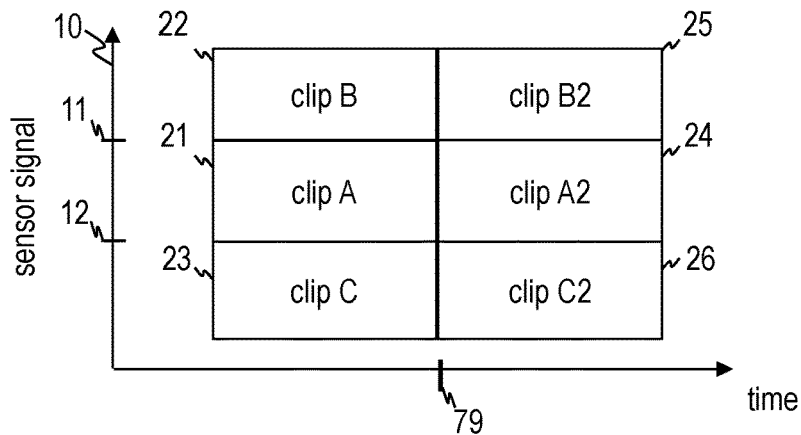
FIG. 12 is a diagram illustrating a time-dependent variation in audio clips during operation of the device according to a preferred embodiment.

FIG. 12 depicts audio clips 21-26 as a function of sensor signal and as a function of the time elapsed from the start of the exercise. Up to a time 79 from the start of the exercise, at least one audio clip 21 and at least one additional audio clip 22, 23 are assigned to different sensor signal sub-ranges that are separated by first and second thresholds 11, 12. As described above, the at least one audio clip 21 may be discontinued and/or the at least one additional audio clip 22, 23 may be initiated in response to the sensor signal reaching or exceeding the first threshold 11 of falling below the second threshold 12, respectively. After time 79, at least one other audio clip 24 and at least one other additional audio clip 25, 26 may be assigned to the different sensor signal sub-ranges that are separated by the first and second thresholds 11, 12. After time 79, play back of the at least one other additional audio clip 25, 26 is initiated when the sensor signal 16 exceeds the first threshold 11 or falls below the second threshold 12. This change in audio clip may be implemented using any one of the techniques explained with reference to FIG. 1 to FIG. 10 above.

The at least one other audio clip 24 may be different from the at least one audio clip 21. Alternatively or additionally, one or both of the at least one other additional audio clips 25, 26 may be different from the at least one additional audio clips 22, 23. All audio clips 21 to 26 may be synchronized, e.g., by respectively having a beat that is synchronized with a common beat.

The at least one audio clip that is output may be changed as a function of time. For illustration, the at least one audio clip 21 may be output prior to time 79 and the at least one other audio clip 24 may be output after time 79, even when the sensor signal remains in the first sensor signal sub-range between the first and second thresholds 11, 12. The change from the at least one audio clip 21 to the at least one other audio clip 24 may, but does not need to involve cross-fading.

While a change in audio output has so far been explained with reference to the evaluation of a single sensor signal, the techniques disclosed herein may also be applied when more than one sensor signal is available for processing by the control device 4. For illustration, one or several sensors may provide a plurality of sensor signals. The plurality of sensor signals may be associated with a single user or with a plurality of users. The control device 4 may take a decision on which audio clips are to be output based on the plurality of sensor signals. For illustration, several audio clips may be arranged in a multi-dimensional array in the parameter space spanned by the plurality of sensor signals. When first and second sensor signals are processed to determine which audio clip(s) is or are to be output, the several audio clips may be arranged in a two-dimensional array of audio clips, as illustrated in FIG. 13.

Figure 13:
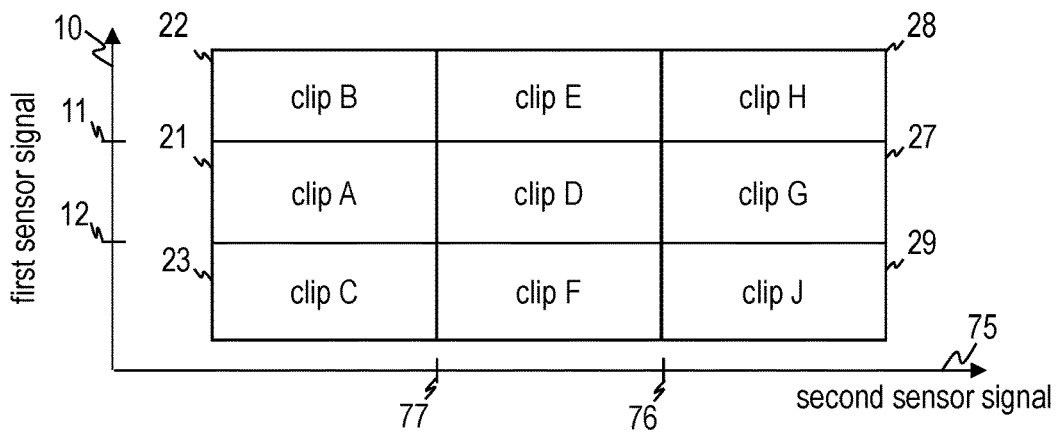
FIG. 13 is a diagram illustrating a two-dimensional array of audio clips that are accessed during operation of the device according to a preferred embodiment.

FIG. 13 illustrates a plurality of audio clips 21-23 and 27-29 in a two-dimensional array. A range of possible values of the first sensor signal is subdivided into a plurality of sensor signal sub-ranges by first and second thresholds 11, 12. A range of possible values of the second sensor signal 75 is subdivided into a plurality of sensor signal sub-ranges by thresholds 76, 77. Both when the first sensor signal reaches one of the first and second thresholds 76, 77 and when the second sensor signal reaches one of the thresholds 76, 77, a change in audio clip(s) may be triggered. For illustration, a change in the second sensor signal that causes the second sensor signal to exceed the threshold 76 may cause the audio clip 27 to be initiated when the first sensor signal is in the first sensor signal sub-range between the thresholds 11, 12. Initiating the audio clip 27 may comprise cross-fading, as described above.

While a two-dimensional arrangement of audio clips is schematically illustrated in FIG. 13, more than two sensor signals may be processed to determine which one of the audio clips is to be output. The control device 4 may evaluate a first, a second, and a third sensor signal and may initiate transitions between audio clips in response to either one of the first, second, and third sensor signals reaching an associated threshold. Accordingly, the plurality of audio clips may be arranged in a three-dimensional array in the three-dimensional parameter space spanned by the first, second, and third sensor signals. More than three sensor signals may be processed to determine which one of the audio clips is to be output. In this case, the several audio clips may be arranged in an N-dimensional array, with N being greater than 3.

The several audio clips have a synchronized beat, irrespective of whether they are arranged in a one-, two-, three- or N-dimensional array, with N being greater than 3. Moreover, any transition between audio clips may be implemented in such a way that the play position from which the at least one additional audio clip is played in response to the sensor signal reaching a threshold depends on the play position of the previously played audio clip at the time at which the at least one additional audio clip is initiated.

While a sensor signal range 10 is being subdivided into three sensor signal sub-ranges by two thresholds throughout the preferred embodiments, more than two thresholds, e.g. three, four, five or more thresholds, may be used to provide more than three sensor signal sub-ranges, e.g. four, five, six or more sensor signal sub-ranges, with respective audio clips being associated therewith. Moreover, more than one audio clip may be associated with one sensor signal sub-range. For example, one audio clip may be played if the sensor signal sub-range is entered from above and another audio clip may be played if the sensor signal sub-range is entered from below.

In any one of the various preferred embodiments disclosed herein, the sensor signal may be provided as an analog or digital value. The sensor signal that is evaluated by the control device to determine which audio clip(s) is or are to be output may be included in a message, which may also include information other than the sensor signal. The message may be a control event message that is generated in response to the sensor signal reaching or exceeding or falling below one of the first and second thresholds 11, 12, for example.

Implementations of a control device according to exemplary embodiments will be explained in more detail with reference to FIG. 14 to FIG. 17.

Figure 14:
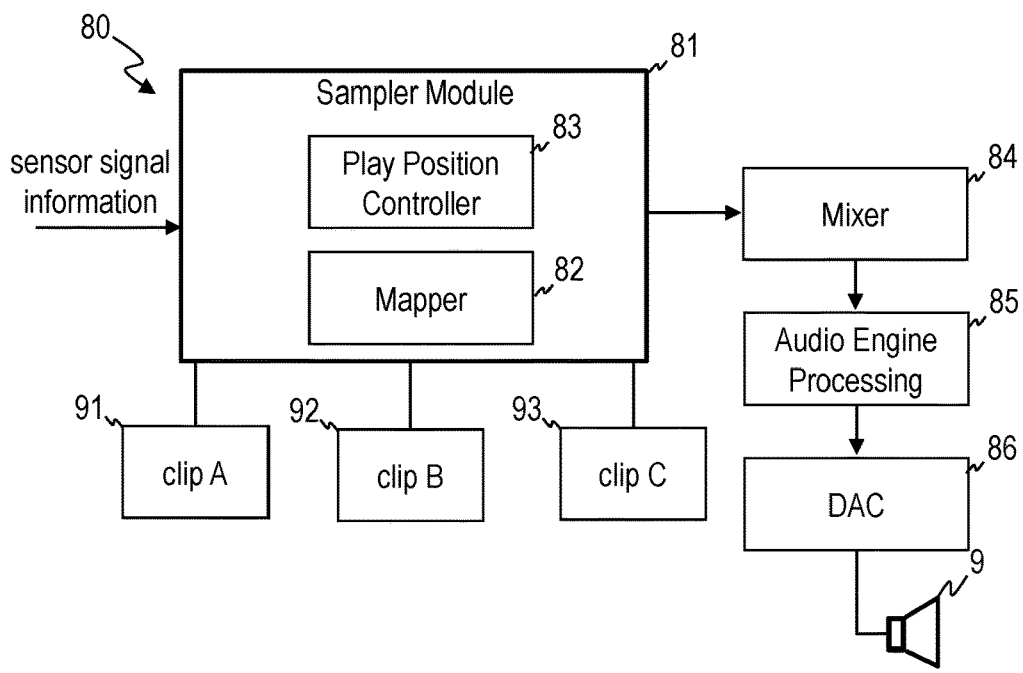
FIG. 14 is a block diagram of a device for controlling acoustic feedback during a physical exercise according to a preferred embodiment.

FIG. 14 is a block diagram representation of a control device 80 that controls the generation of audio feedback in response to a sensor signal. The control device 80 comprises a sampler module 81. The sampler module 81 may comprise at least one integrated circuit. The sampler module 81 may be operative to obtain audio data for a current DSP block. The audio data may respectively include audio data from one of several audio clips 91-93. The sampler module 81 may provide the audio data to a mixer module 84. The mixer module 84 may mix audio samples from the at least one audio clip 21 and the at least one additional audio clip 22, 23 during a cross-fade, for example. More generally, the mixer module 84 may be configured to calculate samples for the current audio block based on the at least one audio clip 21, the at least one additional audio clip 22, 23, or a combination of both, depending on whether only the least one audio clip 21, only the at least one additional audio clip 22, 23, or both are to be output. The mixer module 84 may calculate the samples for the current audio block. An audio engine processing module 85 may receive the samples of the audio block from the mixer module 84. The audio engine processing module 85 may be configured to control a sound card, set a master volume of the sound card, and/or allow sound generated by other routines to be output in addition to the samples provided by the sampler module 81. The audio block holds the samples that are sent to the DAC 86 to produce audible sound.

The sampler module 81 may receive a sensor signal. The sensor signal may be included in an event message generated internally by the control device. The sensor signal may be a value that may be set by one module of a computer program, e.g., a module that polls the sensor or a buffer in which the sensor output is stored. The sensor signal may be read out by another module of the computer program. The sensor signal may be a parameter that is indicative of the sensor output. The parameter indicative of the sensor output may represent an absolute value of the sensor output (i.e., it may reflect an absolute position value, for example). Alternatively, the parameter indicative of the sensor output may represent a speed at which the sensor output reached its current value, i.e., may indicate a rate of change of the sensor (i.e., it may reflect a velocity derived from a change in sensor output of a position sensor, for example). In the latter case, the parameter indicative of the sensor signal may be comparable to the MIDI parameter "velocity". The parameter that is indicative of the sensor signal may have floating point precision, double precision, or may be an integer, long, or long long value. The parameter that is indicative of the sensor signal may be normalized to have values between zero and one.

The sampler module 81 comprises a mapper 82 that handles the selection of the correct audio data for playback in response to the incoming sensor signal information. As described above, the mapper 82 may determine whether an audio clip is to be discontinued and/or which at least one additional audio clip is to be initiated, respectively as a function of the sensor signal. Each one of the several audio clips 91-93 may respectively be associated with a range of sensor signal values. The association between the several audio clips and the range of sensor signal values may, but does not need to be static. For illustration, the association between the several audio clips and the ranges of sensor signal values may vary as a function of time, as described with reference to FIG. 12 above. If an incoming sensor signal has a value in a sensor signal sub-range, the mapper 82 will select audio data from one of the audio clips 91-93. The audio data will be selected from the one of the audio clips 91-93 that is associated with the sensor signal sub-range.

Alternatively or additionally, the thresholds 11, 12 do not need to be static. The thresholds 11, 12 may be varied as a function of one or several of: a sensor input, as a function of time, as a result of a pattern recognition procedure applied to a movement pattern, and/or a result of environmental parameters that may be unrelated to the performance of the physical exercise. The positions or movements of real world objects or virtual reality objects surrounding the user, temperature, lighting conditions, and/or other ambient conditions are exemplary for such environmental parameters.

The sampler module 81 may also comprise a play position controller 83. The play position controller 83 ensures that the audio data for the current DSP block from one or several audio clips stays in synchronization. To this end, the play position controller 83 is operative to determine an offset play position that determines from which play position the at least one additional audio clip is output. The offset play position is determined based on the play position of the previously output at least one audio clip, which was output already prior to the sensor signal reaching the threshold. The play position controller 83 may take into account the ratio of the lengths of the at least one audio clip and the at least one additional audio clip that is initiated if the different audio clips have different lengths. Alternatively or additionally, the play position controller 83 may determine an offset play position based on a global count, e.g., using the techniques described with reference to FIG. 11.

Two types of buffers may respectively be provided for the at least one audio clip and the at least one additional audio clip. A first buffer may save the original audio data. A second buffer may hold a range of the samples from the first buffer. The second buffer can be used to loop the original audio clip or parts of it. The length of the second buffer may initially be set equal to the length of the first buffer. The data in the first buffer may be prepared to fit into a global duration of a measure at the current tempo. This can be done either by a suitable selection of the audio clips or by applying a time stretcher function that causes the audio clip to fit into the global duration of a measure at the current tempo. If the audio data in the first buffer is already at the correct tempo and has a length that is not a multiple of the length of a beat, missing audio data at the end of the buffer can be filled with silence. If the audio data of the audio clip is too long compared to a reference number of beats or compared to a reference number of samples, the excess length can be ignored. In the latter case, the last audio samples of the second buffer may be used for interpolating between the end and the beginning of the audio data to provide smooth looping and to prevent clicks or other artifacts.

Alternatively, a single buffer may be provided. At least two different playheads may be used to read from the same buffer. In this case, the loop may be a sub-range of an audio file. The sub-range may be defined by means of a start sample value and a loop length. The loop length may define the number of samples to be read. When the playhead has read the desired number of samples, an event is triggered which sets the playhead back to the start sample value. In this manner, a single buffer may be used to store audio data from the audio clip and audio data from the at least one additional audio clip.

The audio clip may be a sub-range of an audio file and the at least one additional audio clip may be another sub-range of the same audio file. I.e., one audio file may be used to derive both the audio clip and the at least one additional audio clip therefrom. In this case, a single buffer may store samples from a single audio file. The audio clip that is discontinued and the at least one additional audio clip that is initiated may be derived from the same audio, using two different playheads, for example.

The various functional blocks of the control device 80 may be implemented in hardware, firmware, software, or a combination thereof. Computer-executable instructions may cause a processor of a computing device or communication terminal to perform at least the functions of the sampler module 81, of the mixer 84, and of the audio engine processing module 85.

Figure 15:
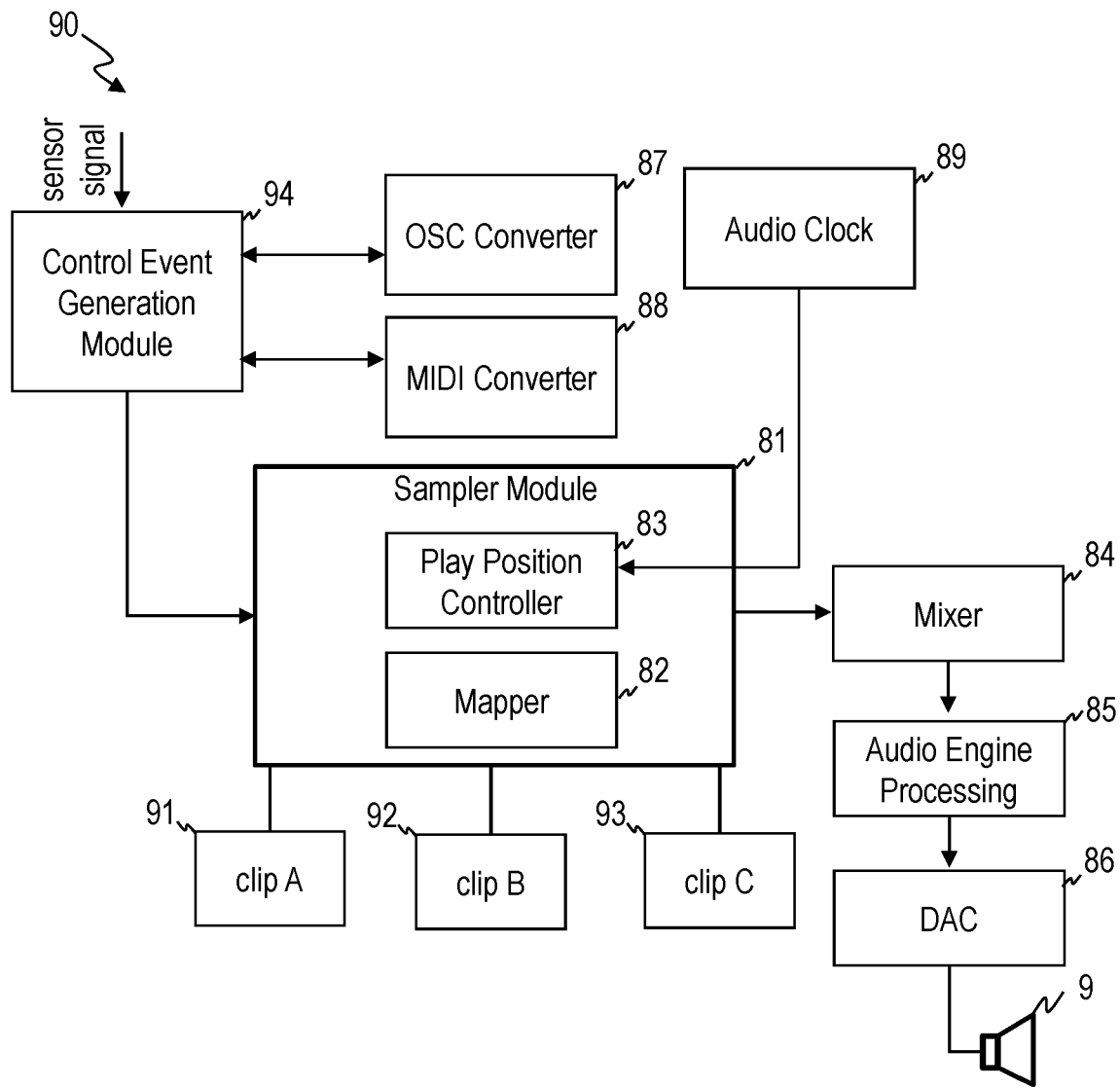
FIG. 15 is a block diagram of a device for controlling acoustic feedback during a physical exercise according to a preferred embodiment.

FIG. 15 is a block diagram representation of a control device 90 that controls the generation of audio feedback in response to a sensor signal. The control device 90 comprises a sampler module 81, a mixer 84, an audio engine processing module 85, and a DAC 86 that may be similar or identical to the respective elements of the control device 80 described with reference to FIG. 14.

The sampler module 81 may be responsive to an event message generated by a control event generation module 94. The event message may include information derived based on the sensor output. The information derived based on the sensor output may comprise information on an absolute value of the sensor output or a rate of change of the sensor output. The control event generation module 94 may monitor the sensor output of the sensor to determine when an event message is to be generated. The control event generation module 94 may actively poll the sensor 3 in pre-defined time intervals, e.g., once per DSP block of the audio data.

More complex polling or data transfer mechanisms may be used. For illustration, the sensor may provide the sensor output to a sensor data buffer. The sensor data buffer may be a buffer of a Bluetooth socket. The control event generation module 94 may poll the sensor data buffer to retrieve the sensor signal.

The sensor may provide the sensor output to the Bluetooth socket or another sensor data buffer in pre-defined time intervals, such as 20 ms. The control event generation module 94 may poll the sensor data buffer at poll times. The poll time of the sensor data buffer may be variable and may depend on various parameters, such as socket load, available computing resources, prioritization of programs executed on a computer, etc.

The control event generation module 94 may provide the sensor signal to the sampler module 81. This may be performed once per DSP block or once per sample.

In an exemplary embodiment, the control event generation module 94 may generate an event message that may include information other than the sensor signal derived from the sensor output. For illustration, the generated event message may include information on a gain. The gain may define a maximum amplitude, i.e., it may define a scaling factor for the envelope of the audio signal. During cross-fading, the gain may be gradually altered based on a fading amplitude, as described with reference to FIG. 5 and FIG. 6. Alternatively or additionally, the event message may include a loop flag. The loop flag may be binary value indicating whether or not the at least one additional audio clip that is initiated in response to the detected change in sensor output is to be played in a loop. Alternatively or additionally, if the loop flag is set to TRUE, the event message may include a loop range that determines a range within an audio buffer that is to be looped. The event message may optionally also include a MIDI note value.

The control device 90 may comprise an audio clock 89. The play position controller 83 may be operative to determine the offset play position based on the audio clock 89. For illustration, the audio clock 89 may have a value that indicates a play position in the at least one audio clip 21 before the sensor signal reaches one of the thresholds 11, 12. The play position may be used to determine the offset play position of the at least one additional audio clip 22, 23.

The control device 90 may comprise a MIDI converter 88. The MIDI converter 88 may be operative to perform data conversion between the MIDI protocol and the events generated by the control event generation module 94. Alternatively or additionally, the control device 90 may comprise an OSC converter 87. The OSC converter 87 may be operative to perform message conversion between the OSC protocol and the event messages generated by the control event generation module 94.

Alternatively or additionally to the control event generation module 94 polling the sensor signal directly from a sensor or from a sensor data buffer, the sensor may be provided to the control event generation module 94 via an OSC interface or a MIDI interface. In this case, the control event generation module 94 may receive the sensor output via the OSC converter 87 or via the MIDI converter 88.

The control devices 80, 90 may respectively be configured to determine whether a transition from at least one audio clip to at least one additional audio clip is to be performed, respectively in dependence on an output signal of a sensor that monitors one or several kinematic parameters of a movement of the user during a physical exercise.

While methods, control devices, and systems have so far generally been described with reference to the monitoring of a single user, the methods, control devices, and systems may also be used to control audio feedback in a group exercise setting in which a plurality of users exercise jointly. One control device or a plurality of control devices may be used to generate the audio feedback for a plurality of users. Each one of the control devices may be operative as described with reference to FIG. 1 to FIG. 15.

Figure 16:
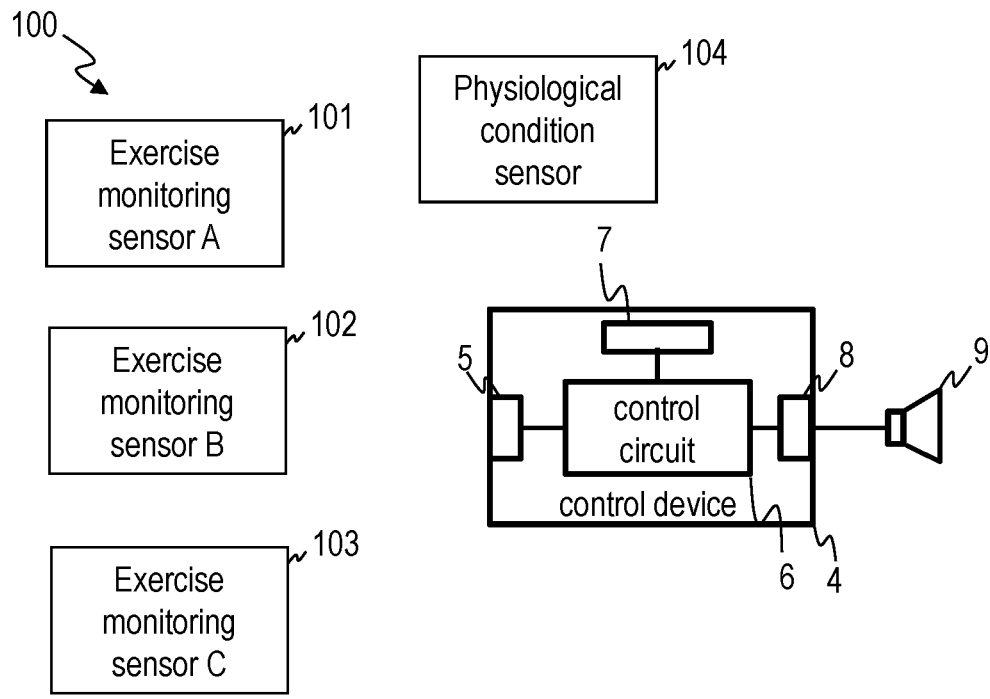
FIG. 16 is a block diagram of a system comprising a device for controlling acoustic feedback during a physical exercise according to a preferred embodiment.

FIG. 16 illustrates a system 100 according to a preferred embodiment. The system 100 comprises a control device 4 generally operative as described with reference to FIG. 1 to FIG. 15. The system 100 comprises a plurality of sensors 101, 102, and 103. At least two of the sensors 101, 102, and 103 may respectively monitor kinematic parameters of the movements of different users. For illustration, a first sensor 101 may monitor at least one kinematic parameter of a movement of a first user during the performance of a physical exercise. A second sensor 102 may concurrently monitor at least one kinematic parameter of a movement of a second user during performance of the physical exercise. Optionally, one or more additional sensor(s) 103 may concurrently monitor at least one kinematic parameter of movements of still further users during performance of the physical exercise.

The control device 4 may have an input interface 5 configured to receive a sensor output from respectively each one of the plurality of sensors 101-103. The control device 4 may be configured to simultaneously output plural audio clips, each respectively associated with one of the plurality of sensors 101-103. If a sensor signal associated with a first sensor 101 indicates that the movement of the first user causes the sensor signal to reach a threshold 11, 12, the control device 4 may cause the at least one audio clip associated with the first sensor 101 to be discontinued and/or at least one additional audio clip associated with the first sensor 101 to be initiated.

In a preferred embodiment, the transition between audio clips associated with the first sensor 101 does not affect the audio clips that are output for the other users and their associated sensors 102, 103. I.e., the control device 4 may control transitions between audio clips independently for each one of the sensor outputs provided by the sensors 101, 102, 103.

In another preferred embodiment, the transition between audio clips associated with the first sensor 101 may simultaneously affect the audio clips that are output for the other users. I.e., when the sensor signal determined from the output signal of the first sensor 101 reaches the first threshold 11 or the second threshold 12, this may not only cause a transition in the clip that is output in dependence on the output signal of the first sensor 101, but may also trigger a change in the clip that is output for at least one of the other users. The plural audio clips may be arranged in a multi-dimensional array in the multi-dimensional parameter space spanned by the sensor signals from the plural sensors 101-103, as described with reference to FIG. 13.

Discontinuing at least one clip and/or initiating at least one additional clip may be triggered in dependence on physical movement of plural users detected by one or several sensors. For illustration, the output signal of the first sensor 101 and the output signal of the second sensor 102 may be evaluated using logical functions that determine whether the movements of first and second users comply with a pre-defined criterion, e.g., by determining whether the movements of different users are coordinated with each other. The at least one additional clip may be selectively initiated only if the movement of the first user and the movement of the second user in combination fulfill a specific criterion. For illustration, the at least one additional clip may be initiated only if a first user performs an exercise having first predetermined movement characteristics and if a second performs an exercise having second predetermined movement characteristics. The first and second predetermined movement characteristics may respectively be detected using pattern matching techniques. The at least one additional clip may be initiated selectively only if the movements of the first and second users exhibit the first and second movement characteristics in a time-correlated manner, e.g., by concurrently moving in a coordinated manner.

In one exemplary implementation, at least a sub-set of the several clips may be selectively activated only if at least two users concurrently perform a reciprocating movement, such as by shaking a body part with a target frequency. For illustration, referring to FIG. 13, instead of or in addition to performing a threshold comparison to thresholds 11, 76, the at least one additional clip 28 may be initiated only if at least two users concurrently shake a body part with a target frequency.

The threshold values for the sensor signal at which transitions between different audio clips are triggered may respectively be different for different sensors 101, 102, 103. For illustration, when the sensors 101-103 are mounted on different types of exercise devices in a group exercise setting, the transitions between audio clips can occur at different movement amplitudes and/or movement velocities, depending on the types of exercise device to which the sensors 101, 102, 103 are respectively mounted.

In any one of the preferred embodiments disclosed herein, the audio clip(s) that are output may not only depend on the kinematic parameters of a movement detected by the sensors 101-103, such as position, velocity, or acceleration of a part of the user's body or part of an exercise device, but may also depend on at least one physiological condition of the user that is different from the kinematic parameter.

Figure 17:
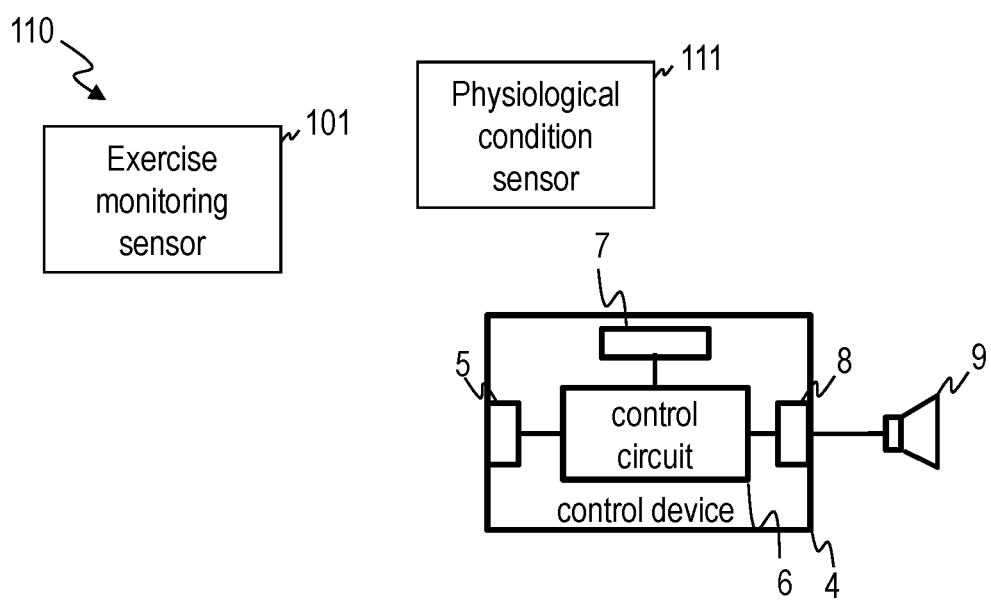
FIG. 17 is a block diagram of a system comprising a device for controlling acoustic feedback during a physical exercise according to a preferred embodiment.

FIG. 17 is a schematic block diagram of a system 110. The system 110 comprises a control device 4 generally operative as described with reference to FIG. 1 to FIG. 16 above. The system 110 comprises a sensor 101 operative to monitor at least one kinematic parameter associated with the user's movement during the physical exercise. The at least one kinematic parameter may comprise one or several of a position, a velocity, or an acceleration of at least a part of the user's body or of at least a part of an exercise device. The system 110 further comprises a physiological condition sensor 111 operative to sense at least one physiological condition of the user during performance of the exercise. The at least one physiological condition may be selected from a group consisting of a breathing rate, a heart rate, and a blood pressure, without being limited thereto.

The control device 4 may control the outputting of audio feedback during the physical exercise both in dependence on a sensor signal that depends on the sensor output of the sensor 101 and based on the sensor output of the physiological condition sensor 111. For illustration, the control device 4 may control transitions between audio clips as a function of the sensor output of the sensor 101. The control device 4 may additionally control the acoustic feedback based on the output signal of the physiological condition sensor 111. For illustration, a beat of the acoustic feedback may be varied so as to have a rate that matches the user's heart rate or breathing rate. Additionally or alternatively, one or several audio clip(s) may be selected based on the recognition of a movement pattern with pattern classification algorithms or other events derived from environmental changes that are unrelated to the movement of the user during the physical exercise.

Figure 18:
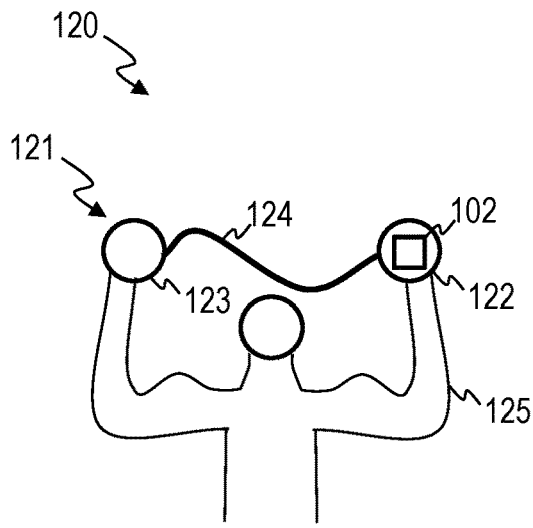
FIG. 18 is a block diagram of a system comprising a device for controlling acoustic feedback during a physical exercise according to a preferred embodiment.
Figure 18:
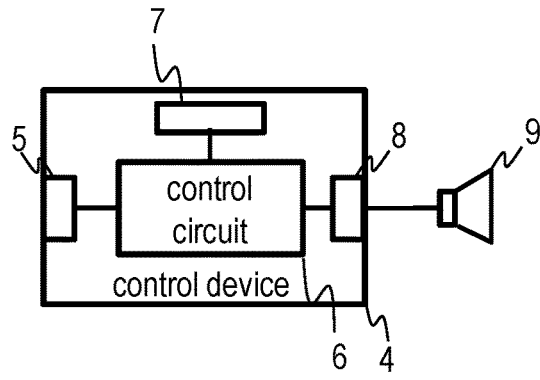

FIG. 18 is a schematic block diagram of a system 120. The system 120 comprises a control device 4 generally operative as described with reference to FIG. 1 to FIG. 17 above. The system 120 comprises an exercise device 121.

The exercise device 121 comprises two objects 122, 123 which are connected to one another by an elastic element 124. The objects 122, 123 may be grips, balls, batons, barbells, or any other kind of objects which may easily be gripped by or held within a hand of a user 125. The elastic element 124 may, e.g., be an elastic band or rope.

A sensor 102 may be arranged on or within at least one of the objects 122, 123. The sensor 102 may comprise an accelerometer and/or a gyrometer and/or a strain gauge and/or a load cell mounted on or within at least one of the two objects 122, 123. Alternatively or additionally, a sensor may be arranged on or in the elastic element 124. The sensor arranged on or in the elastic element 124 may be operative to sense tensile or compressive load applied onto the elastic element 124, an absolute expansion or compression of the elastic element 124, or a relative expansion or compression of the elastic element 124 normalized to the length of the elastic element 124. The sensor arranged on or in the elastic element 124 may comprise a strain gauge and/or a load cell.

The sensor(s) 102 provided on one or both of the objects 122, 123 and/or the elastic element 124 may respectively be configured to provide a sensor signal to the control device 4. The sensor signal may comprise plural signals or data items, thereby representing a vector in a multi-dimensional sensor signal space. The plural signals or data items may comprise at least two pieces of data selected from a group consisting of position, velocity, acceleration, coordinate axis, movement direction, and force. In addition, or alternatively, the sensor signal may be related to the velocity of moving one or both of the objects, or the velocity of the expansion of the elastic element, and/or the direction in which the objects are being moved, and/or the direction in which the elastic element is being expanded.

Figure 19:
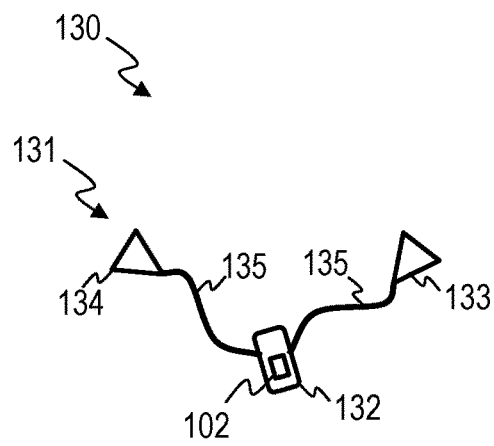
FIG. 19 is a block diagram of a system comprising a device for controlling acoustic feedback during a physical exercise according to a preferred embodiment.
Figure 19:
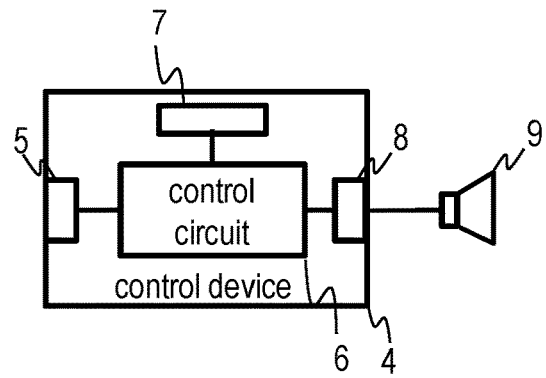

FIG. 19 is a schematic block diagram of a system 130. The system 130 comprises a control device 4 generally operative as described with reference to FIG. 1 to FIG. 18 above. The system 130 comprises an exercise device 131.

The exercise device 131 comprises at least three objects 132, 133, 134 which are connected to one another by at least one elastic element 135. The objects 133, 134 may be grips, balls, batons, barbells, or any other kind of objects which may easily be gripped by or held within a hand of a user. The object 132 may be interposed between the objects 133, 134 along the elastic element 135 and may, but does not need to be configured for being held by the user during performance of an exercise. Similarly to the exercise device 121, one or several sensor(s) 102 may be provided on or within the at least three objects 132, 133, 134 and/or on or within the at least one elastic element 135. The elastic element 135 may comprise one or several elastic bands or ropes. The sensor(s) 102 provided on one, two or three of the objects 132, 133, 134 and/or the elastic element 135 may respectively be configured to provide a sensor signal to the control device 4. The sensor signal may comprise plural data items, thereby representing a vector in a multi-dimensional sensor signal space. The plural data items may comprise at least two pieces of data selected from a group consisting of position, velocity, acceleration, coordinate axis, movement direction, and force. In addition, or alternatively, the sensor signal may be related to the velocity of moving one or both of the objects, or the velocity of the expansion of the elastic element, and/or the direction in which the objects are being moved, and/or the direction in which the elastic element 135 is being expanded.

The elastic band or rope 124, 135 of the exercise devices 121 and 131 may respectively have a length in its relaxed state of between 10 cm and 1 m, e.g., of between 20 cm and 60 cm. When subject to admissible loads, the length of the elastic element may change by less than 30 cm, preferably by less than 20 cm, e.g., by less than 10 cm or less than 5 cm. The elastic element may be configured to be stretched to at least twice of its relaxed length applying a stretching force in the range between 20 N and 200 N, preferably between 40 N and 100 N.

While the exercise devices 121, 131 are configured to be used in such a manner that a tensile load is exerted onto the exercise devices 121, 131, the system according to an embodiment may alternatively or additionally comprise an exercise device that has an elastic element configured to be compressed by a user. Alternatively or additionally, the exercise device may have an element that is configured to be deflected. For illustration rather than limitation, the exercise device may be a flex bar configured to be deflected transversely to a longitudinal axis of the flex bar. The flex bar may have small dimensions for use in office or residential environments, for example. A sensor signal indicative of the compressive movement of an elastic element and/or the deflection of a flex bar may be processed by the control device 4, using the techniques described in detail with reference to FIG. 1 to FIG. 19.

The object 132 may be a sensor configured to be releasably attached to an elastic member, such as an elastic band, as will be explained in more detail with reference to FIGS. 22 and 23.

Figure 20:
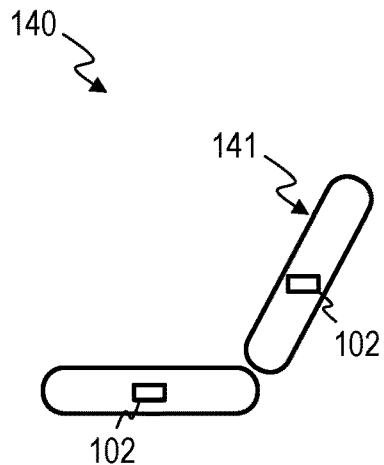
FIG. 20 is a block diagram of a system comprising a device for controlling acoustic feedback during a physical exercise according to a preferred embodiment.
Figure 20:
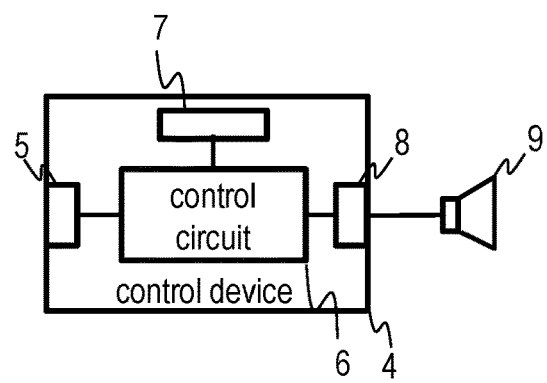

FIG. 20 is a schematic block diagram of a system 140. The system 140 comprises a control device 4 generally operative as described with reference to FIG. 1 to FIG. 19 above. The system 140 comprises a seat 141. The seat 141 may be a vehicle seat, e.g., an automotive vehicle seat or an aircraft seat. The seat 141 may be an office furniture or residential furniture. The seat 141 may be an office chair, for example.

The seat 141 may comprise one or several sensors 102. A sensor 102 may be arranged on or within at least one part of the seat 141. A plurality of sensors 102 are preferably mounted to or installed within the seat 141. The sensor 102 may comprise an accelerometer and/or a gyrometer and/or a strain gauge and/or a load cell to detect movement of the seat occupant and/or forces exerted by the seat occupant onto the seat.

The sensor(s) 102 provided on the seat 141 may respectively be configured to provide a sensor signal to the control device 4. The sensor signal may comprise plural signals or data items, thereby representing a vector in a multi-dimensional sensor signal space. The plural signals or plural data items comprise at least two pieces of data selected from a group consisting of position, velocity, acceleration, coordinate axis, movement direction, and force. The control device 4 may process the sensor signal(s) to determine whether an audio clip is to be discontinued and/or whether at least one additional audio clip is to be initiated.

Figure 21:
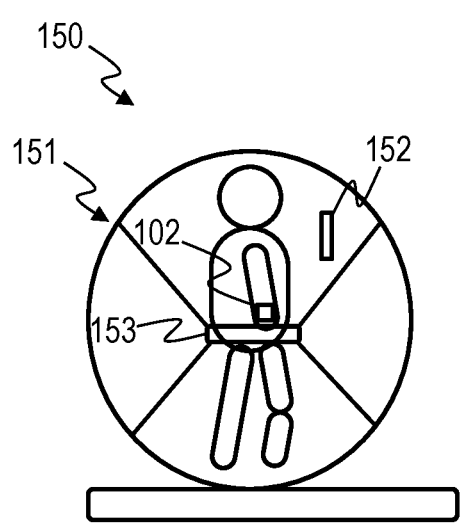
FIG. 21 is a block diagram of a system comprising a device for controlling acoustic feedback and for providing visual signals during a physical exercise according to a preferred embodiment.
Figure 21:
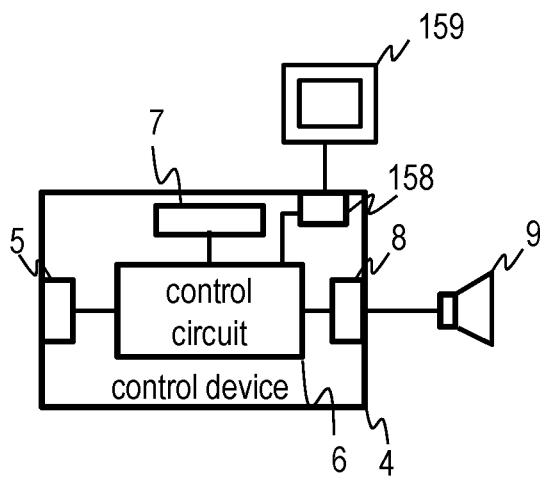

FIG. 21 is a schematic block diagram of a system 150. The system 150 comprises a control device 4 generally operative as described with reference to FIG. 1 to FIG. 20 above. The system 150 comprises an exercise device or recreational device 151.

The exercise device 151 or recreational device 151 may be configured to suspend a user on the exercise device 151 or recreational device 151. The exercise device 151 or recreational device 151 may be configured such that the user's orientation in three-dimensional real world space relative to a base position of the exercise device 151 or recreational device 151 may be controlled. The exercise device 151 or recreational device 151 may comprise plural swivel mechanisms that allow the user to be positioned in three-dimensional real world space, with at least a user's height axis (i.e., an axis from the user's feet to the user's head) being orientable in three-dimensional real world space by the exercise device 151 or recreational device 151. At least two angular coordinates of the user's height axis may be positionable by the exercise device 151 or recreational device 151. The exercise device 151 or recreational device 151 may comprise a belt system 153, such as a hip belt system, which allows the user to be suspended in the exercise device 151 or recreational device 151 in such a manner that the user is suspended in the exercise device 151 or recreational device 151.

The exercise device 151 or recreational device 151 may be controllable via an input element 152, such as a joystick. The exercise device 151 or recreational device 151 may be controllable via the input element 152 to set the user's orientation in three-dimensional real world space. Alternatively or additionally, the exercise device 151 or recreational device 151 may be controlled in an automatic manner. The exercise device 151 or recreational device 151 may be configured to automatically transition through a sequence of orientations and/or movements in three-dimensional real world space.

The system 150 comprises at least one sensor 102 which may be mounted on the exercise device 151 or recreational device 151, which may be a wearable sensor, or which may be another sensor such as a camera positioning system or another non-contact sensor, or a combination thereof. The sensor 102 may provide the sensor signal to the control device 4.

Depending on the orientation along which the user is suspended by the exercise device 151 or recreational device 151, different parts of the body may be effectively exercised. The control device 4 may monitor and record the orientations for which physical exercises have been performed. The control device 4 may provide suggestions or instructions on the orientation(s) of the user in three-dimensional real world space for which future exercises should be performed, or can choose different positions/movement progressions in an automated fashion. The control device 4 may have an interface 158 for controlling an optical output device 159, which may be a screen of a dedicated optical output device, a communication terminal, or another optical output device.

Visual signals may be provided via the optical output device 159. The visual signals may comprise information on the physical exercise that is to be performed and/or on the parts of the body that require further exercise and/or on the way in which the user is to be suspended in an exercise device for the physical exercise. Alternatively or additionally, the visual signals may comprise visual effects. The visual effects may comprise graphical animations. The visual signal may be controlled by the same sensor signal(s) that control the audio feedback.

The control device 4 may provide acoustic feedback, as has been described above.

Figure 22:
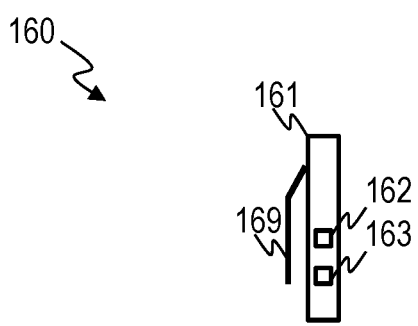
FIG. 22 is a block diagram of a system comprising a device for controlling acoustic feedback during a physical exercise according to a preferred embodiment.
Figure 22:
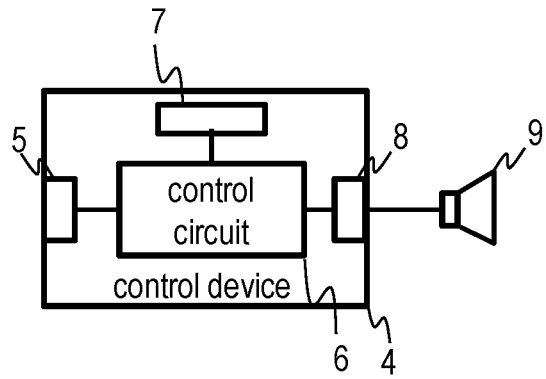

FIG. 22 is a schematic block diagram of a system 160. The system 160 comprises a control device 4 generally operative as described with reference to FIG. 1 to FIG. 21 above. The system 160 comprises a sensor 161.

The sensor 161 is configured to be attached to an elastic member of an exercise device. The sensor 161 may be configured for releasable attachment to an elastic rope or elastic band, without requiring modification or disassembly of the elastic rope or elastic band. The sensor 161 may have a housing and a bracket 169 or other attachment mechanism that is operative to secure the sensor 161 on the elastic member, e.g., by using a friction fit. The bracket 169 may be biased towards the housing of the sensor 161 to retain an elastic member of an exercise device between the bracket 169 and an abutment surface on the housing of the sensor 161. The bracket or other attachment mechanism can be an integral part of the mechanism to measure the expansion of the elastic member of the exercise device.

The sensor 161 may be configured to provide at least one sensor signal to the control device 4. The sensor signal(s) may be indicative of a tension or compression of the elastic member and/or of an orientation of the elastic member to which the sensor 161 is mounted. The sensor 161 may comprise a first sensing unit 162 configured to sense a tension or compression of the elastic member to which the sensor 161 is mounted. The first sensing unit 162 may be configured to sense the tension of an elastic band, for example. The first sensing unit 162 may comprise a strain gauge and/or may use non-contact sensing techniques, such as optical sensing, to determine the tension. The sensor 161 may comprise a second sensing unit 163 configured to sense an orientation of the sensor 161, which is indicative of an orientation of the elastic member to which the sensor 161 is mounted. The second sensing unit 163 may comprise an accelerometer, for example, or other orientation sensor.

Various advantages are attained by use of a sensor 161 that can be clipped or otherwise releasably attached to an elastic member of an exercise device. The sensor 161 can be used on conventional elastic bands or ropes and allows conventional bands or ropes to be used in association with the control device 4. The sensor 161 can be fitted onto conventional elastic bands or ropes without requiring disassembly or other modification of the conventional elastic bands or ropes, other than releasably attaching the sensor 161 onto the elastic band or rope.

Figure 23:
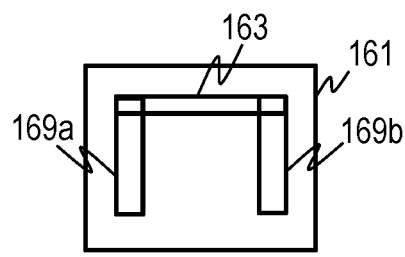
FIG. 23 is a plan view of a sensor that may be used in the system of FIG. 22.

FIG. 23 is a plan view of an implementation of a sensor 161 that may be used in the system of FIG. 22. The sensor 161 comprises a plurality of brackets 169a, 169b for attachment to an elastic member. The plurality of brackets 169a, 169b may be spaced apart along the direction in which the elastic member extends along the sensor 161 when the sensor 161 is mounted to the elastic member. The plurality of brackets 169a, 169b may comprise two or more brackets that are each attached to a strain gauge 163. The strain gauge 163 may be a strip-shaped strain gauge. The plurality of brackets 169a, 169b is configured to transfer tension or compression in the elastic member is transmitted onto the strain gauge 163. Each of the plurality of brackets 169a, 169b may be configured to engage a part of the elastic member in a friction fit, so that tension or compression in the elastic member is transferred onto the strain gauge 163.

In order to accommodate the various types of sensors, a calibration routine may be performed, as will be explained in more detail with reference to FIG. 24.

Various types of sensors may be used in the methods and systems according to embodiments. For illustration, the control device according to an embodiment may be configured to control the provision of audio feedback based on a wide variety of different movements, as has been explained above. Different kinds of sensors may be used, depending on the type of movement that is to be monitored. For illustration, a non-contact distance measuring sensor (which may be based on laser measurement techniques or infrared sensing) may be particularly suitable for measuring substantially linear movements. The non-contact distance measuring sensor may be positioned so as to be spaced by less than a threshold distance from the user. An acceleration sensor or other orientation sensor can be used to measure the orientation relative to the gravity vector. Suitable sensors may also be operative to measure a movement in free space. For illustration, stereo camera systems may be used for 3D tracking in free space.

Figure 24:
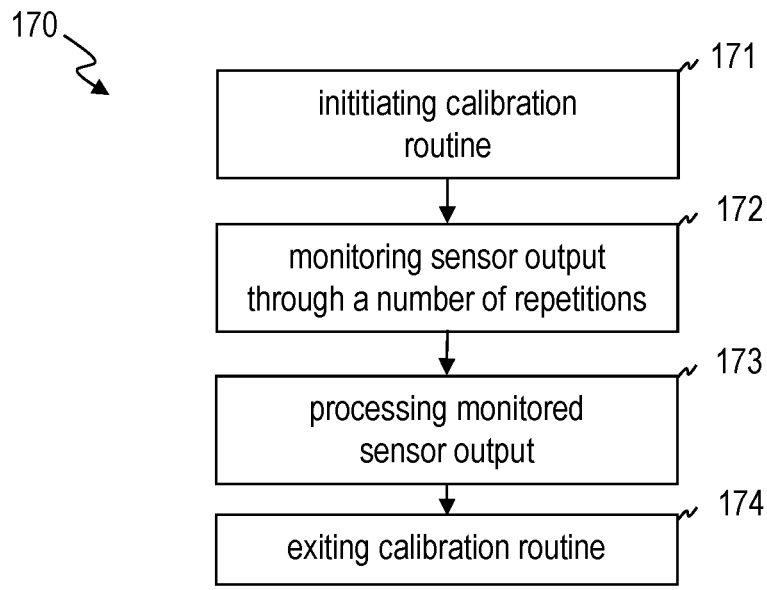
FIG. 24 is a flow chart of a method according to an embodiment which comprises a calibration routine.

FIG. 24 is a flow chart of a method 170 according to an embodiment. At step 171, a calibration routine is initiated. The calibration routine may be performed prior to outputting audio signals. Alternatively or additionally, the calibration routine may be performed while audio signals are output. At step 172, a sensor output is monitored in the calibration routine. The sensor output may be monitored through a minimum number of repetitions of a user's movement in the calibration routine. The minimum number of repetitions may depend on the type of sensor that is used and/or may depend on whether the user's movement is a cyclical movement. For illustration, if the sensor measures a one-dimensional movement, the sensor output may be monitored through at least one repetition of the movement to determine a start point and an end point of the physical movement. If the sensor detects movement in free space, more than two repetitions of the movement may be monitored in the calibration routine for enhanced accuracy. When the physical exercise involves a cyclical movement pattern, as may be the case for running or cycling, a different calibration routine may be used. For illustration, the height to which the user lifts his/her legs when running, the frequency at which the user lifts his/her legs when running, and/or the pedaling frequency when cycling may be monitored in the calibration routine. The acceleration may additionally be monitored. Various values can be derived from a sensor output, e.g., an activity value that may be used for calibration.

At step 173, the sensor output monitored in the calibration routine may be processed. For illustration, a processing routine for processing a sensor output or several sensor outputs to generate sensor signals that are then compared with the first and second thresholds may be calibrated based on the sensor signal monitored in the calibration routine. The sensor output monitored in the calibration routine may be used to determine a scaling factor with which a sensor output is multiplied before it is compared to the first and second thresholds. Alternatively or additionally, more complex mapping techniques may be used to process a sensor output to generate the sensor signal therefrom. For illustration, different functions or tables may be used to map a sensor output onto a sensor signal which is then compared to the first and second thresholds. The functions or tables may be adjusted in dependence on the sensor output monitored in the calibration routine. The plurality of audio clips may be selected in dependence on the sensor output monitored in the calibration routine. Alternatively or additionally, the plurality of audio clips may be selected in dependence on the sensor output monitored in the calibration routine.

The calibration may be performed so as to provide an improved audio feedback that matches the user's physical exercise in an optimum manner.

At step 174, the calibration routine may be exited.

After step 174, audio feedback may be provided during a physical exercise, using the results of the calibration routine. Steps 171 to 174 may be executed prior to outputting audio feedback or in parallel with the provision of audio feedback. The calibration routine may run in the background, such that audio feedback based on a former or a default calibration is audible during the calibration routine. The provision of audio feedback may be implemented using any one of the techniques described with reference to FIG. 1 to FIG. 23.

The first and second thresholds may be adjusted while a calibrated movement is carried out, i.e., after calibration. This allows an adaptation to be performed for specific exercises or for specific exercise devices.

Figure 25:
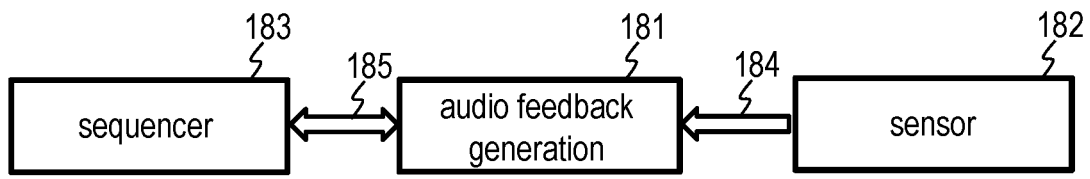
FIG. 25 is a block diagram of a system according to a preferred embodiment.

FIG. 25 is a block diagram of a system according to a preferred embodiment. The system provides an interface

185 between an audio feedback generation module 181 and a sequencer 183. The audio feedback generation module 181 may be configured to output an audio signal in response to the received sensor signal 184 from a sensor 182. The output audio signal comprises one or more audio clips, as has been explained above.

The audio feedback generation module 181 and the sequencer 183 may be implemented by hardware, software, firmware or a combination thereof. The audio feedback generation module 181 and the sequencer 183 may be apps executed on the same device, e.g., on a mobile communication terminal or another portable computing device.

The interface may be used for various purposes. For illustration, the sequencer may provide one, at least two, or all of the several audio clips to the audio feedback generation module via the interface. Alternatively or additionally, the sequencer may provide one or several data streams, e.g. MIDI, to the audio feedback generation module via the interface. The data streams may be used to control the audio feedback generation module. Alternatively or additionally, the audio signal or data relating to the audio signal may be provided by the audio feedback generation module to the sequencer via the interface.

The audio feedback generation module may operate as a plug-in for sequencer, or vice versa. When the audio feedback generation module operates as plug-in for sequencer, the time of use of audio feedback generation module may be monitored for billing purposes, for example.

The interface may be a ReWire, Virtual Studio Technology (VST), or Ableton Link interface, without being limited thereto.

The methods, devices, and systems according to preferred embodiments of the invention are capable of playing back audio material that provides musical features like beat, rhythm, harmony, or melody. The audio material can be played in a loop. The audio material may be synchronized to a common tempo, such as by synchronizing the several audio clips to a common beat. The content of the output audio signal can be manipulated in real time and on the fly, while maintaining a play position and staying synchronized to the common tempo and the current beat. When cross-fading is used, quick changes in the sensor output do not cause clicks or other artifacts like audible distortion in the output audible feedback.

The audio material may be synchronized to a common tempo and phase, such as by synchronizing the several audio clips to a common beat.

In any one of the preferred embodiments disclosed herein, the audio clips may be or may comprise sampled audio data (e.g., snippets of recorded or synthesized audio), MIDI data, OSC messages, or data in a different format such as a proprietary format.

In any one of the preferred embodiments disclosed herein, the thresholds do not need to be static. The thresholds may be varied as a function of a sensor signal or as a function of time, or as a result of a pattern recognition procedure applied to a movement pattern, or as a result of environmental parameters that may be unrelated to the performance of the physical exercise. The positions or movements of real world objects and/or of virtual reality objects surrounding the user, temperature, lighting conditions, and/or other ambient conditions are exemplary for such environmental parameters.

The methods, devices, and systems according to preferred embodiments of the invention trigger audio clips or combinations of audio clips when acoustic signals are output during a physical exercise. The user does not have to worry about the exact onset of the transition from one audio clip to another one within the current rhythmic context. The methods, devices, and systems make it seem as though all audio material is running in synchronization from the beginning, and the user may vary and combine different audio materials in a spontaneous fashion. The methods, devices, and systems enable the user to switch between several audio clips at any point in time. The user is therefore enabled to change the sound in accordance with his or her preference at any point in time, without having to worry about synchronization with the current acoustic signal. The methods, devices, and systems preserve the capability of creating rapid and sudden changes of the audio feedback that is a salient feature of experiencing musical agency, i.e., to ensure that excitation patterns of movement are reflected by corresponding excitation patterns of the audio signal.

In the methods, devices, and systems according to preferred embodiments of the invention, the control device is capable of distinguishing between increasing and decreasing sensor outputs. Different actions may be triggered depending on whether a sensor signal enters a given sensor signal sub-range from its lower threshold or its upper threshold, respectively. The different actions can include, for example, setting a loop range through which the at least one additional audio clip is looped in dependence on whether the sub-range is entered from its lower boundary or its upper boundary, respectively.

The methods, devices, and systems according to preferred embodiments of the invention may be implemented using a control device that executes instruction code which causes the control device to perform the method according to any one of the preferred embodiments disclosed herein. The control device may comprise a stationary or portable computer, a portable communication terminal such as a cellular phone, tablet, personal digital assistant or other communication terminal, or an application specific computing device. The computing device may comprise an embedded Linux computer.

The methods, devices, and systems for controlling acoustic feedback during a physical exercise disclosed herein enable the user to easily generate interesting acoustic feedback that is considered to be motivating, without requiring the user to synchronize a beat of the acoustic feedback with the movements carried out during the physical exercise. The methods, devices, and systems allow a large space of possible sounds and combinations of sounds to be explored by the user during an exercise. The methods, devices, and systems may be used for a physical exercise performed individually by a single user, but are also particularly suitable for group exercise settings in which a plurality of users exercise jointly.

The invention claimed is:

1. A method of providing acoustic feedback during a physical exercise, the method comprising:
providing several audio clips having a synchronized beat, wherein the several audio clips having a synchronized beat exhibit repeated temporal events that relate to identical intervals therebetween or a recurring pattern of maximum acoustic amplitude or timbre events in temporal alignment with a common beat;
capturing a sensor signal by a sensor attached to an elastic member of an exercise device;
receiving the sensor signal from the sensor, the sensor signal having a sensor signal range divided by first and second thresholds into at least three sensor signal sub-ranges; and outputting an audio signal in response to the received sensor signal, the output audio signal comprising one or more of the audio clips;

wherein, when the received sensor signal exceeds the first threshold, at least one of the one or more audio clips is discontinued and/or at least one additional audio clip of the audio clips is initiated in synchronization with the one or more audio clips; and wherein, when the received sensor signal falls below the second threshold, at least one of the one or more audio clips is discontinued and/or at least one additional audio clip of the audio clips is initiated in synchronization with the one or more audio clips.

2. The method of claim 1, wherein discontinuing at least one of the one or more audio clips comprises fading out the at least one of the one or more audio clips.

3. The method of claim 1, wherein initiating at least one additional audio clip of the audio clips comprises fading in the at least one additional audio clip.

4. The method of claim 1, wherein initiating at least one additional audio clip comprises determining an offset play position from which the at least one additional audio clip is played.

5. The method of claim 4, wherein the offset play position of the at least one additional audio clip is determined based on a ratio of a length of the at least one of the one or more audio clips to a length of the at least one additional audio clip or by performing a modulo operation.

6. The method of claim 1, wherein the common beat is adjusted based on
at least one physiological parameter of a person performing the physical exercise and/or
the sensor signal and/or
at least one environmental parameter.

7. The method of claim 1, wherein outputting an audio signal comprises playing the one or more audio clips in a loop until the received sensor signal exceeds the first threshold or falls below the second threshold.

8. The method of claim 1, further comprising adapting the one or more audio clips or the additional audio clip as a function of:
an elapsed time since the start of the physical exercise; and/or
movement characteristics detected by the sensor; and/or
at least one physiological parameter of a person performing the physical exercise.

9. The method of claim 1, wherein the several audio clips comprise sampled audio data, MIDI clips, OSC clips, or clips of a proprietary format.

10. The method of claim 1, wherein the sensor is mounted to an exercise device, or wherein the sensor comprises a wearable sensor.

11. The method of claim 1, wherein initiating at least one additional audio clip comprises determining an offset play position from which the at least one additional audio clip is played, wherein the offset play position of the at least one additional audio clip is determined based on a play position of the at least one of the one or more audio clips or on a global count at the time at which the received sensor signal exceeds the first threshold or falls below the second threshold or based on a play position of the at least one of the one or more audio clips at the time at which at least one additional audio clip of the audio clips is initiated.

12. The method of claim 1, further comprising: outputting visual signals.

13. The method of claim 12, wherein a) the visual signals comprise animations or information on the physical exercise that is to be performed and/or information on parts of a body that require further exercise and/or information on the way in which a user should be suspended in an exercise device for the physical exercise and/or b) the physical exercise is performed on an exercise device or recreational device that allows a user's orientation in three-dimensional real world space to be controlled.

14. The method of claim 1, wherein the sensor is configured to be clipped onto the elastic member.

15. The method of claim 1, wherein the sensor is configured to detect a tension and/or compression of the elastic member, and/or wherein the sensor is configured to detect an orientation of the elastic member.

16. The method of claim 1, further comprising: monitoring a sensor output in a calibration routine.

17. The method of claim 16, wherein the sensor output is monitored through a minimum number of repetitions of a user's movement in the calibration routine, wherein the minimum number of repetitions depends on
the type of sensor that is used and/or
whether the user's movement is a cyclical movement.

18. The method of claim 1,
wherein the several audio clips are provided by a sequencer and/or
wherein the audio signal or data relating to the audio signal is provided to the sequencer and/or
wherein the sequencer provides control information to a device for controlling the acoustic feedback during the physical exercise.

19. A computer program comprising software code adapted to perform the method according to claim 1 when executed by a processor.

20. A system, comprising:
a sensor responsive to a user's actions during a physical exercise, the sensor having a sensor signal range;
an exercise device comprising an elastic member, wherein the sensor is attached to the elastic member of the exercise device; and
a device for controlling acoustic feedback during a physical exercise, the device comprising:
a memory storing several audio clips having a synchronized beat, wherein the several audio clips having a synchronized beat exhibit repeated temporal events that relate to identical intervals therebetween or a recurring pattern of maximum acoustic amplitude or timbre events in temporal alignment with a common beat;
an input to receive the sensor signal having the sensor signal range divided by first and second thresholds into at least three sensor signal sub-ranges; and
a control circuit to control outputting of an audio signal in response to the received sensor signal, the output audio signal comprising one or more of the audio clips output in a synchronized manner;
the control circuit being configured to
cause at least one of the one or more audio clips to be discontinued and/or at least one additional audio clip of the audio clips to be initiated in synchronization with the one or more audio clips when the sensor signal exceeds the first threshold; and
cause at least one of the one or more audio clips to be discontinued and/or at least one additional audio clip of the audio clips to be initiated in synchronization with the one or more audio clips when the sensor signal falls below the second threshold.

21. The system of claim 20, wherein the sensor comprises a wearable sensor or at least one camera.

22. The system of claim 20, wherein the exercise device comprises two objects which are connected to one another by an elastic element, wherein the sensor comprises an accelerometer and/or a gyrometer and/or a strain gauge and/or a load cell.

* * * * *